(12) United States Patent
Pang et al.

(10) Patent No.: US 12,635,885 B2
(45) Date of Patent: May 26, 2026

(54) SYSTEMS AND METHODS FOR IMAGE REORIENTATION FOR ENDOSCOPIC IMAGING

(71) Applicant: Stryker Corporation, Kalamazoo, MI (US)

(72) Inventors: Chien Mien Pang, San Jose, CA (US); Eric Charles Huynh, San Ramon, CA (US)

(73) Assignee: Stryker Corporation, Portage, MI (US)

( * ) Notice: Subject to any disclaimer, the term of this patent is extended or adjusted under 35 U.S.C. 154(b) by 223 days.

(21) Appl. No.: 17/086,133

(22) Filed: Oct. 30, 2020

(65) Prior Publication Data

US 2021/0127948 A1 May 6, 2021

Related U.S. Application Data

(60) Provisional application No. 62/929,349, filed on Nov. 1, 2019.

(51) Int. Cl.
A61B 5/00 (2006.01)
A61B 1/00 (2006.01)
(Continued)

(52) U.S. Cl.
CPC ........ A61B 5/0077 (2013.01); A61B 1/00009 (2013.01); A61B 1/00105 (2013.01);
(Continued)

(58) Field of Classification Search
CPC ............ A61B 1/00009; A61B 1/00045; A61B 1/00105; A61B 1/00188; A61B 1/042;
(Continued)

(56) References Cited

U.S. PATENT DOCUMENTS

| | | | |
|---|---|---|---|
| 3,636,366 A | * 1/1972 | Sheldon .................. | H01J 31/28 |
| | | | 250/214 VT |
| 4,187,422 A | * 2/1980 | Zoltan .................. | G01D 18/006 |
| | | | 250/203.1 |

(Continued)

FOREIGN PATENT DOCUMENTS

| | | |
|---|---|---|
| EP | 0655710 A2 | 5/1995 |
| WO | 2014/106059 A2 | 7/2014 |

OTHER PUBLICATIONS

International Search Report and Written Opinion mailed Apr. 16, 2021, directed to International Application No. PCT/US2020/058278, 26 pages.

(Continued)

*Primary Examiner* — Peter D Le
(74) *Attorney, Agent, or Firm* — Morrison & Foerster LLP

(57) ABSTRACT

A method for medical imaging, the method including receiving light from a scene at a camera assembly that comprises at least one reflecting optical element and an imaging sensor assembly; reflecting light received by the camera assembly from the scene toward the imaging sensor assembly via the at least one reflecting optical element, wherein reflecting the light causes the scene to be at least one of inverted and reverted at the imaging sensor assembly; focusing the reflected light onto the imaging sensor assembly with at least one focusing optical element; transmitting image data generated from the focused light from the imaging sensor assembly to a camera controller; and generating by the camera controller a non-inverted and non-reverted image of the scene from the data generated by the imaging sensor assembly.

30 Claims, 11 Drawing Sheets

(51) Int. Cl.

| | |
|---|---|
| *A61B 1/04* | (2006.01) |
| *A61B 1/045* | (2006.01) |
| *H04N 5/262* | (2006.01) |
| *H04N 23/55* | (2023.01) |
| *H04N 23/50* | (2023.01) |

(52) U.S. Cl.

CPC .......... *A61B 1/00188* (2013.01); *A61B 1/042* (2013.01); *A61B 1/045* (2013.01); *H04N 5/2628* (2013.01); *H04N 23/55* (2023.01); *H04N 23/555* (2023.01)

(58) Field of Classification Search

CPC ... A61B 1/045; A61B 2505/05; A61B 5/0077; A61B 5/067; H04N 2005/2255; H04N 5/2254; H04N 5/23229; H04N 5/2628; H04N 1/00; H04N 3/00; H04N 5/00; H04N 7/00; H04N 9/00; H04N 11/00; H04N 13/00; H04N 17/00; H04N 19/00; H04N 21/00; H04N 2101/00; H04N 2201/00; H04N 2209/00; H04N 2213/00

See application file for complete search history.

(56) References Cited

U.S. PATENT DOCUMENTS

| | | | | |
|---|---|---|---|---|
| 4,199,232 A | * | 4/1980 | Olodort | G03B 21/10 |
| | | | | 359/211.2 |
| 4,615,590 A | * | 10/1986 | Alvarez | G02B 27/64 |
| | | | | 396/529 |
| 4,890,159 A | | 12/1989 | Ogiu | |
| 4,993,819 A | * | 2/1991 | Moorhouse | G02B 23/14 |
| | | | | 359/638 |
| 5,298,939 A | * | 3/1994 | Swanson | G03F 7/70275 |
| | | | | 355/71 |
| 5,727,236 A | * | 3/1998 | Frazier | G02B 13/0095 |
| | | | | 359/822 |
| 5,747,813 A | * | 5/1998 | Norton | G01B 11/0625 |
| | | | | 250/339.11 |
| 5,762,605 A | | 6/1998 | Cane et al. | |
| 7,471,310 B2 | | 12/2008 | Amling et al. | |
| 7,821,530 B2 | | 10/2010 | Amling et al. | |
| 11,215,426 B1 | * | 1/2022 | Campbell | F41G 11/003 |
| 2001/0017661 A1 | * | 8/2001 | Shono | G03B 13/08 |
| | | | | 348/E5.025 |
| 2002/0038074 A1 | * | 3/2002 | Hakamata | A61B 1/00186 |
| | | | | 600/178 |
| 2004/0207901 A1 | * | 10/2004 | Kaneko | G02B 26/0825 |
| | | | | 359/290 |
| 2005/0286883 A1 | * | 12/2005 | Abe | H04N 1/2112 |
| | | | | 396/266 |
| 2006/0241496 A1 | | 10/2006 | Fengler | |
| 2008/0225134 A1 | | 9/2008 | Amling et al. | |
| 2011/0109971 A1 | * | 5/2011 | Beach | G02B 17/026 |
| | | | | 359/896 |
| 2012/0193423 A1 | * | 8/2012 | Samek | G06K 7/109 |
| | | | | 235/462.01 |
| 2014/0121459 A1 | * | 5/2014 | Hoeg | A61B 1/00165 |
| | | | | 600/109 |
| 2015/0279061 A1 | * | 10/2015 | Kutsuna | G06T 7/0012 |
| | | | | 382/131 |
| 2015/0341536 A1 | * | 11/2015 | Huang | H04N 23/80 |
| | | | | 348/208.2 |
| 2016/0192823 A1 | * | 7/2016 | Yasunaga | A61B 1/00066 |
| | | | | 600/109 |
| 2017/0020364 A1 | * | 1/2017 | Hofer | A61B 1/00009 |
| 2018/0007322 A1 | * | 1/2018 | Kojo | A61B 1/00172 |
| 2018/0161024 A1 | * | 6/2018 | Davis | A61B 1/00188 |
| 2020/0060526 A1 | * | 2/2020 | Toth | G02B 23/2476 |

OTHER PUBLICATIONS

Invitation to Pay Additional Fees, and where Applicable, Protest Fee and Partial Search Result mailed Feb. 26, 2021, directed to International Application No. PCT/US2020/058278; 19 pages.

International Preliminary Report on Patentability dated May 3, 2022, directed to International Application No. PCT/US2020/058278; 16 pages.

1 Office Action dated Jan. 9, 2024, directed to EP Application No. 20 811 491.8; 5 pages.

* cited by examiner

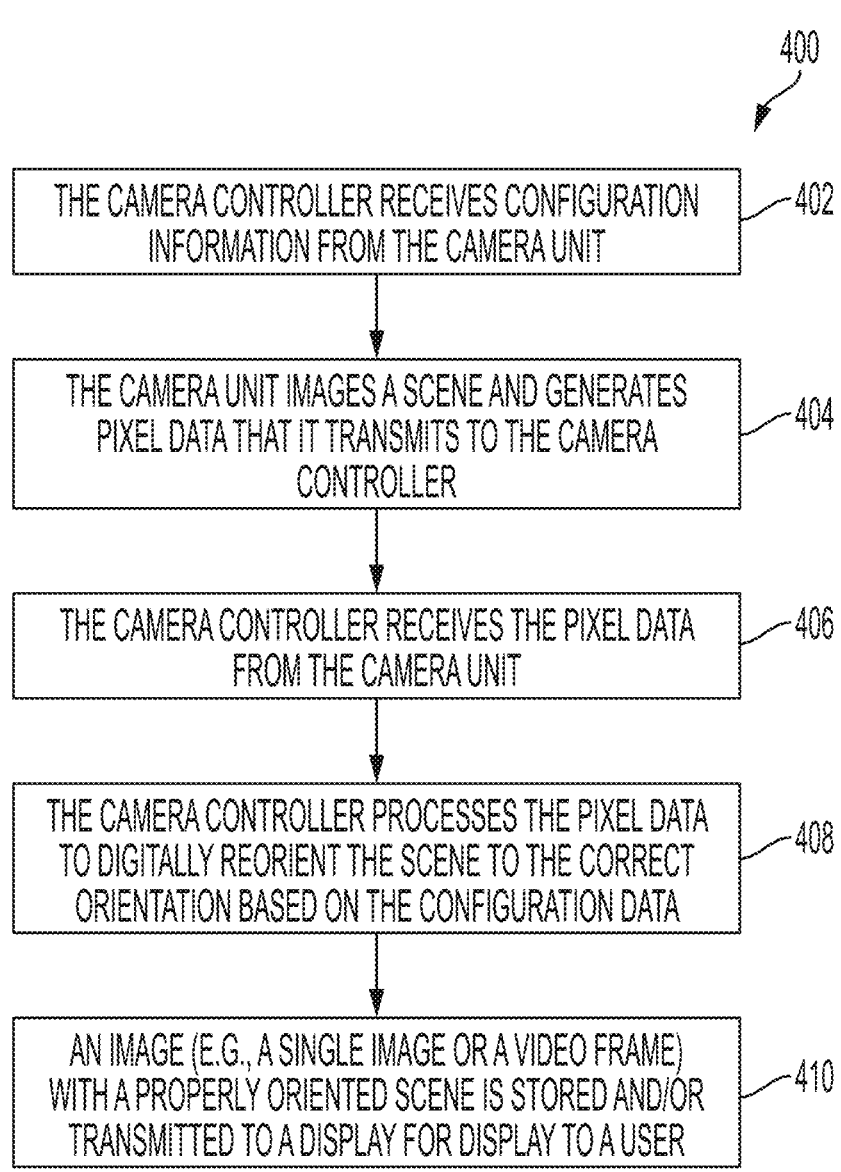

400

THE CAMERA CONTROLLER RECEIVES CONFIGURATION INFORMATION FROM THE CAMERA UNIT ——402

THE CAMERA UNIT IMAGES A SCENE AND GENERATES PIXEL DATA THAT IT TRANSMITS TO THE CAMERA CONTROLLER ——404

THE CAMERA CONTROLLER RECEIVES THE PIXEL DATA FROM THE CAMERA UNIT ——406

THE CAMERA CONTROLLER PROCESSES THE PIXEL DATA TO DIGITALLY REORIENT THE SCENE TO THE CORRECT ORIENTATION BASED ON THE CONFIGURATION DATA ——408

AN IMAGE (E.G., A SINGLE IMAGE OR A VIDEO FRAME) WITH A PROPERLY ORIENTED SCENE IS STORED AND/OR TRANSMITTED TO A DISPLAY FOR DISPLAY TO A USER ——410

FIG. 4

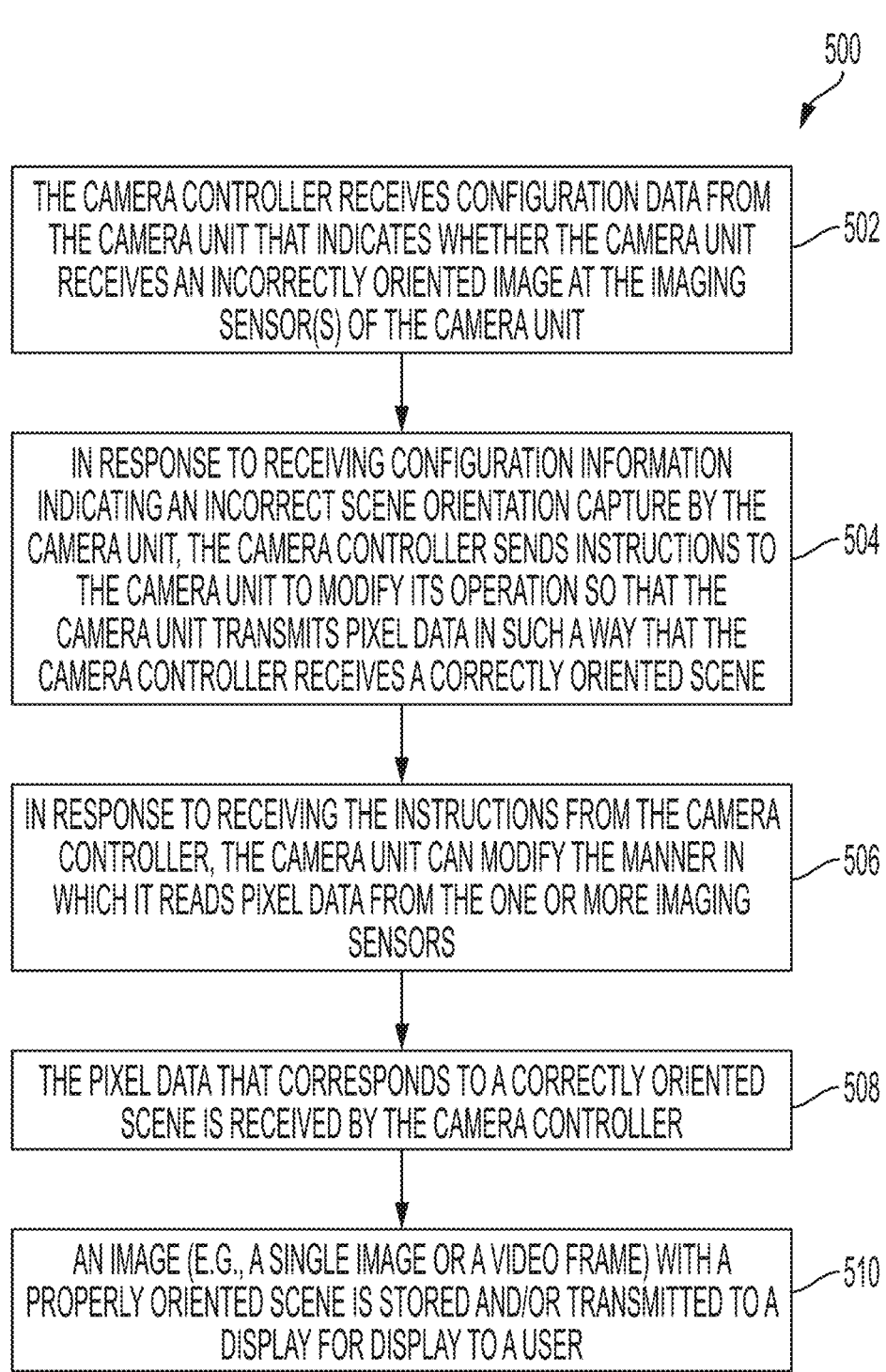

500

THE CAMERA CONTROLLER RECEIVES CONFIGURATION DATA FROM THE CAMERA UNIT THAT INDICATES WHETHER THE CAMERA UNIT RECEIVES AN INCORRECTLY ORIENTED IMAGE AT THE IMAGING SENSOR(S) OF THE CAMERA UNIT — 502

IN RESPONSE TO RECEIVING CONFIGURATION INFORMATION INDICATING AN INCORRECT SCENE ORIENTATION CAPTURE BY THE CAMERA UNIT, THE CAMERA CONTROLLER SENDS INSTRUCTIONS TO THE CAMERA UNIT TO MODIFY ITS OPERATION SO THAT THE CAMERA UNIT TRANSMITS PIXEL DATA IN SUCH A WAY THAT THE CAMERA CONTROLLER RECEIVES A CORRECTLY ORIENTED SCENE — 504

IN RESPONSE TO RECEIVING THE INSTRUCTIONS FROM THE CAMERA CONTROLLER, THE CAMERA UNIT CAN MODIFY THE MANNER IN WHICH IT READS PIXEL DATA FROM THE ONE OR MORE IMAGING SENSORS — 506

THE PIXEL DATA THAT CORRESPONDS TO A CORRECTLY ORIENTED SCENE IS RECEIVED BY THE CAMERA CONTROLLER — 508

AN IMAGE (E.G., A SINGLE IMAGE OR A VIDEO FRAME) WITH A PROPERLY ORIENTED SCENE IS STORED AND/OR TRANSMITTED TO A DISPLAY FOR DISPLAY TO A USER — 510

FIG. 5

SYSTEMS AND METHODS FOR IMAGE REORIENTATION FOR ENDOSCOPIC IMAGING

CROSS-REFERENCE TO RELATED APPLICATIONS

This application claims the benefit of U.S. Provisional Application No. 62/929,349, filed Nov. 1, 2019, the entire contents of which are hereby incorporated by reference herein.

FIELD OF THE INVENTION

The present invention generally relates to medical imaging, and more specifically to endoscopic imaging.

BACKGROUND OF THE INVENTION

An endoscopic camera system typically includes a camera head connected to camera control unit (CCU). The CCU processes input image data from the image sensor of the camera and then outputs the image data for display. Typically, the camera head has a coupler assembly attached or mounted to the camera head. The coupler mounts endoscopes to the camera head for internal visualization of the body during minimally invasive surgical procedures.

The camera head and coupler can be different for various surgical specialties or procedures. Thus, the camera head and coupler may be specialized, having different forms and functionalities. An example of such a specialization is for a urology and/or ENT camera head. One end of the coupler, which connects to an endoscope, is oriented at a right angle relative to the image sensing plane of the imaging sensor in the camera head. The image plane provided by the endoscope is then effectively oriented at a right angle (i.e., 90°) from the image sensing plane of the imaging sensor. Due to this orientation of the image plane, the coupler typically includes an optical component that redirects the image light 90°.

Typically, a reflecting component is used to redirect the light by 90°. Various prisms have been used for this purpose, including pentaprisms and Amici roof prisms. A pentaprism is a five-sided reflecting prism that utilizes two of those surfaces to reflect the beam inside the prism twice. The pentaprism allows the image to be reflected and transmitted through the prism without inverting or reverting the image (i.e., no image flips). A roof prism is a triangular shaped reflecting prism that includes a "roof" section on the long edge of the prism. The image is reflected off of the two angled surfaces that create the "roof" of the prism, resulting in a reversion (lateral flip) of the image. Additionally, due to the 45° long edge of the prism, the image is also inverted (vertical flip) as it passes through the prism. The combination of a reversion and an inversion of the image, ultimately results in the image rotation 180°. This simplifies the requirements for the camera to interpret the data, as the camera sensor can be mounted upside-down (180° rotated from normal) to match the upside-down prism image.

The repeated reflections and increase in optical path length associated with both pentaprisms and roof prisms can decrease image quality. Further, manufacturing tolerances must be minimized so that the image is accurately reflected.

SUMMARY OF THE INVENTION

According to some embodiments, systems and methods can include a camera controller that can detect the configuration of a connected endoscopic camera head and control the camera head and/or digitally process image data received from the camera head to generate images in which the scene is correctly oriented even when the scene is incorrectly oriented as received by one or more imaging sensors of the camera head. According to some embodiments, the ability of the camera controller to control the camera head and/or digitally process image data to change the scene orientation relative to its orientation at the camera head, enables a right angle camera head that has a right angle prism in which light is redirected 90° via a single reflection, which can improve image quality and can reduce manufacturing costs.

According to some embodiments, the camera controller can detect the configuration of the camera via data stored in the camera head and/or in a cable connecting the camera head to the camera controller. This configuration data can indicate that the camera head is a right angle camera head. According to some embodiments, based on the camera head configuration information, the camera controller can instruct the camera head to read imaging sensor pixels in reverse order so that the scene is flipped relative to how it is received by the one or more imaging sensors, which can correct for flipping of the scene caused by the single reflection within the camera head. In other embodiments, the camera controller can digitally process the image data by, for example, reversing the order of pixels within each image to flip the scene.

According to some embodiments, a camera head can be configured with one or more sensors for detecting an orientation of the camera head and the camera controller can control the camera head and/or process the image data received from the camera head to maintain the scene in a correct orientation (relative to the expectations of the user) when the camera head is turned upside down. This can provide the user with the ability to turn the camera head upside down for improved handling of the endoscopic camera assembly during surgery without having the scene flip upside down on the display.

According to some embodiments, a medical imaging system includes a camera assembly comprising: an imaging sensor assembly comprising at least one imaging sensor for imaging a scene; at least one focusing optical element for focusing light onto the imaging sensor assembly; at least one reflecting optical element for reflecting light received by the camera assembly from the scene toward the at least one focusing optical element, wherein reflecting the light causes the scene to be at least one of inverted and reverted at the imaging sensor assembly; and a camera controller configured to generate a non-reverted and non-inverted image of the scene based on image data received from the imaging sensor.

In any of these embodiments, the camera controller can be configured to control the camera assembly so that data is read from the at least one imaging sensor in reverse with respect to at least one dimension of the at least one imaging sensor.

In any of these embodiments, the camera controller can be configured to reorder the image data received from the imaging sensor to generate the image of the scene.

In any of these embodiments, the camera controller can be configured to detect a configuration of the camera assembly based on camera assembly configuration data stored in the camera assembly and generate the image of the scene based on the camera assembly configuration data.

In any of these embodiments, the camera controller can be connected via a cable to a camera head comprising the imaging sensor assembly and the camera assembly configuration data can be stored in the cable or in the camera head.

In any of these embodiments, the one or more reflecting optical elements can be configured to invert the scene.

In any of these embodiments, the imaging sensor assembly can be configured so that the at least one imaging sensor receives a reverted scene.

In any of these embodiments, the one or more reflecting optical elements can be configured to reflect the light only once.

In any of these embodiments, the one or more reflecting optical elements can include a right angle prism.

In any of these embodiments, the camera assembly can be configured for mounting a scope at a right angle orientation relative to an optical axis of the at least one focusing optical element.

In any of these embodiments, a camera head can include the imaging sensor assembly and the endoscope can be removably mounted to the camera head.

In any of these embodiments, when the scope is mounted to the camera assembly, an optical axis of the scope can be perpendicular to the optical axis of the at least one focusing optical element.

In any of these embodiments, the one or more reflecting optical elements can be configured to reflect light at a right angle.

In any of these embodiments, the one or more reflecting optical elements can be configured to reflect light at an angle that is in a range from 80° to 100°.

In any of these embodiments, the imaging sensor assembly can include at least one prism for reflecting the focused light to the at least one imaging sensor.

According to some embodiments, a method for medical imaging includes receiving light from a scene at a camera assembly that comprises at least one reflecting optical element and an imaging sensor assembly; reflecting light received by the camera assembly from the scene toward the imaging sensor assembly via the at least one reflecting optical element, wherein reflecting the light causes the scene to be at least one of inverted and reverted at the imaging sensor assembly; focusing the reflected light onto the imaging sensor assembly with at least one focusing optical element; transmitting image data generated from the focused light from the imaging sensor assembly to a camera controller; and generating by the camera controller a non-inverted and non-reverted image of the scene from the data generated by the imaging sensor assembly.

In any of these embodiments, the method can include receiving camera configuration data at the camera controller and generating the correctly oriented image of the scene based on the camera configuration data being indicative of incorrect orientation of the scene at the imaging sensor assembly.

In any of these embodiments, the method can include reading data from at least one imaging sensor of the imaging sensor assembly in reverse with respect to at least one dimension of the at least one imaging sensor.

In any of these embodiments, the method can include reordering the image data received from the imaging sensor to generate the image of the scene.

In any of these embodiments, the method can include detecting a configuration of the camera assembly based on camera assembly configuration data stored in the camera assembly and generating the image of the scene based on the camera assembly configuration data.

In any of these embodiments, the camera controller can be connected via a cable to a camera head that includes the imaging sensor assembly and the camera assembly configuration data can be stored in the cable or in the camera head.

In any of these embodiments, the one or more reflecting optical elements can invert the scene.

In any of these embodiments, the method can include receiving a reverted scene at the imaging sensor assembly.

In any of these embodiments, the one or more reflecting optical elements can be configured to reflect the light only once.

In any of these embodiments, the one or more reflecting optical elements can include a right angle prism.

In any of these embodiments, the camera assembly can be configured for mounting a scope at a right angle orientation relative to an optical axis of the at least one focusing optical element.

In any of these embodiments, a camera head can include the imaging sensor assembly and the endoscope can be removably mounted to the camera head.

In any of these embodiments, when the scope is mounted to the camera assembly, an optical axis of the scope can be perpendicular to the optical axis of the at least one focusing optical element.

In any of these embodiments, the one or more reflecting optical elements can be configured to reflect light at a right angle.

In any of these embodiments, the one or more reflecting optical elements can be configured to reflect light at an angle that is in a range from 80° to 100°.

In any of these embodiments, the imaging sensor assembly can include at least one prism for reflecting the focused light to the at least one imaging sensor.

According to some embodiments, a method for medical imaging includes receiving camera configuration data for a camera at a camera controller via a connection between the camera controller and the camera; determining based on the camera configuration data whether the camera is configured to reflect a scene onto at least one imaging sensor of the camera that is at least one of inverted and reverted; in accordance with a determination that the camera is configured to reflect the scene onto at least one imaging sensor of the camera that is at least one of inverted and reverted, controlling the camera and processing image data received from the camera according to a first imaging process to generate a non-inverted and non-reverted image of a scene; and in accordance with a determination that the camera is configured to reflect the scene onto the at least one imaging sensor of the camera in a correct orientation, controlling the camera and processing image data received from the camera according to a second imaging procedure that is different than the first imaging procedure to generate an image of the scene in the correct orientation.

In any of these embodiments, the first imaging process can include controlling the camera to transmit image data associated with the scene to the camera controller in accordance with a reverse pixel read with respect to at least one pixel dimension; and generating the non-inverted and non-reverted image of the scene from the image data.

In any of these embodiments, the first imaging process can include receiving image data that is associated with at least one of an inverted and a reverted scene from the camera at the camera controller; and digitally processing the image data so that the image of the scene is non-inverted and non-reverted.

In any of these embodiments, the second imaging process can include receiving image data that is associated with a correctly oriented scene from the camera at the camera controller; and generating the image of the scene in the correct orientation from the image data.

According to some embodiments, a camera controller for medical imaging includes one or more processors; memory; and one or more programs stored in the memory and executable by the one or more processors for: receiving camera configuration data for a camera at the camera controller via a connection between the camera controller and the camera; determining based on the camera configuration data whether the camera is configured to reflect a scene onto at least one imaging sensor of the camera that is at least one of inverted and reverted; in accordance with a determination that the camera is configured to reflect the scene onto at least one imaging sensor of the camera that is at least one of inverted and reverted, controlling the camera and processing image data received from the camera according to a first imaging process to generate a non-inverted and non-reverted image of a scene; and in accordance with a determination that the camera is configured to reflect the scene onto the at least one imaging sensor of the camera in a correct orientation, controlling the camera and processing image data received from the camera according to a second imaging procedure that is different than the first imaging procedure to generate an image of the scene in the correct orientation.

In any of these embodiments, the first imaging process can include controlling the camera to transmit image data associated with the scene to the camera controller in accordance with a reverse pixel read with respect to at least one pixel dimension; and generating the non-inverted and non-reverted image of the scene from the image data.

In any of these embodiments, the first imaging process includes receiving image data that is associated with at least one of an inverted and a reverted scene from the camera at the camera controller; and digitally processing the image data so that the image of the scene is non-inverted and non-reverted.

In any of these embodiments, the second imaging process can include receiving image data that is associated with a correctly oriented scene from the camera at the camera controller; and generating the image of the scene in the correct orientation from the image data.

According to some embodiments, a medical imaging system includes a camera assembly that includes: an imaging sensor assembly comprising at least one imaging sensor for imaging a scene, and an angular orientation sensor for sensing an angular orientation of the camera assembly relative to an optical axis of the imaging sensor assembly; and a camera controller configured to receive camera assembly orientation information generated by the orientation sensor and to generate an image having a reoriented scene in response to receiving orientation information from the camera assembly that indicates that the camera assembly is in a predetermined range of angular orientations relative to the optical axis of the imaging sensor assembly.

In any of these embodiments, the angular orientation sensor can include at least one of a gyroscope and an accelerometer.

In any of these embodiments, the camera controller can be configured to reorient the scene 180°.

In any of these embodiments, the camera controller can be configured to reorient the scene so that the scene in the image is right-side-up when the camera assembly is upside-down.

In any of these embodiments, the camera controller can be configured to generate an image having a reoriented scene by instructing the camera assembly to change a pixel read order.

In any of these embodiments, the camera controller can be configured to generate an image having a reoriented scene by reordering image data received from the imaging sensor assembly.

In any of these embodiments, the predetermined range of angular orientations can be +/−90° from upside-down.

According to some embodiments, a method for medical imaging includes imaging a scene at an imaging sensor assembly of a camera assembly, and sensing an angular orientation of the camera assembly relative to an optical axis of the imaging sensor assembly; receiving imaging data from the imaging sensor assembly at a camera controller; receiving camera assembly orientation data at the camera controller; and generating an image having a reoriented scene in response to receiving camera assembly orientation that indicates that the camera assembly is in a predetermined range of angular orientations relative to the optical axis of the imaging sensor assembly.

In any of these embodiments, sensing the angular orientation can include sensing the angular orientation via at least one of a gyroscope and an accelerometer.

In any of these embodiments, the method can include reorienting the scene 180°.

In any of these embodiments, the method can include reorienting the scene so that the scene in the image is right-side-up when the camera assembly is upside-down.

In any of these embodiments, the method can include instructing the camera assembly to change a pixel read order.

In any of these embodiments, the method can include reordering image data received from the imaging sensor assembly.

In any of these embodiments, the predetermined range of angular orientations can be +/−90° from upside-down.

BRIEF DESCRIPTION OF THE FIGURES

The invention will now be described, by way of example only, with reference to the accompanying drawings, in which:

FIG. 4 illustrates a method for generating images having a correctly oriented scene by digitally reorienting the scene at the camera controller, according to some embodiments;

FIG. 5 illustrates a method for generating images having correctly oriented scenes by modifying the camera unit operation such that the camera unit transmits image data to the camera controller in accordance with a correctly oriented scene, according to some embodiments;

DETAILED DESCRIPTION

Figure 1A:
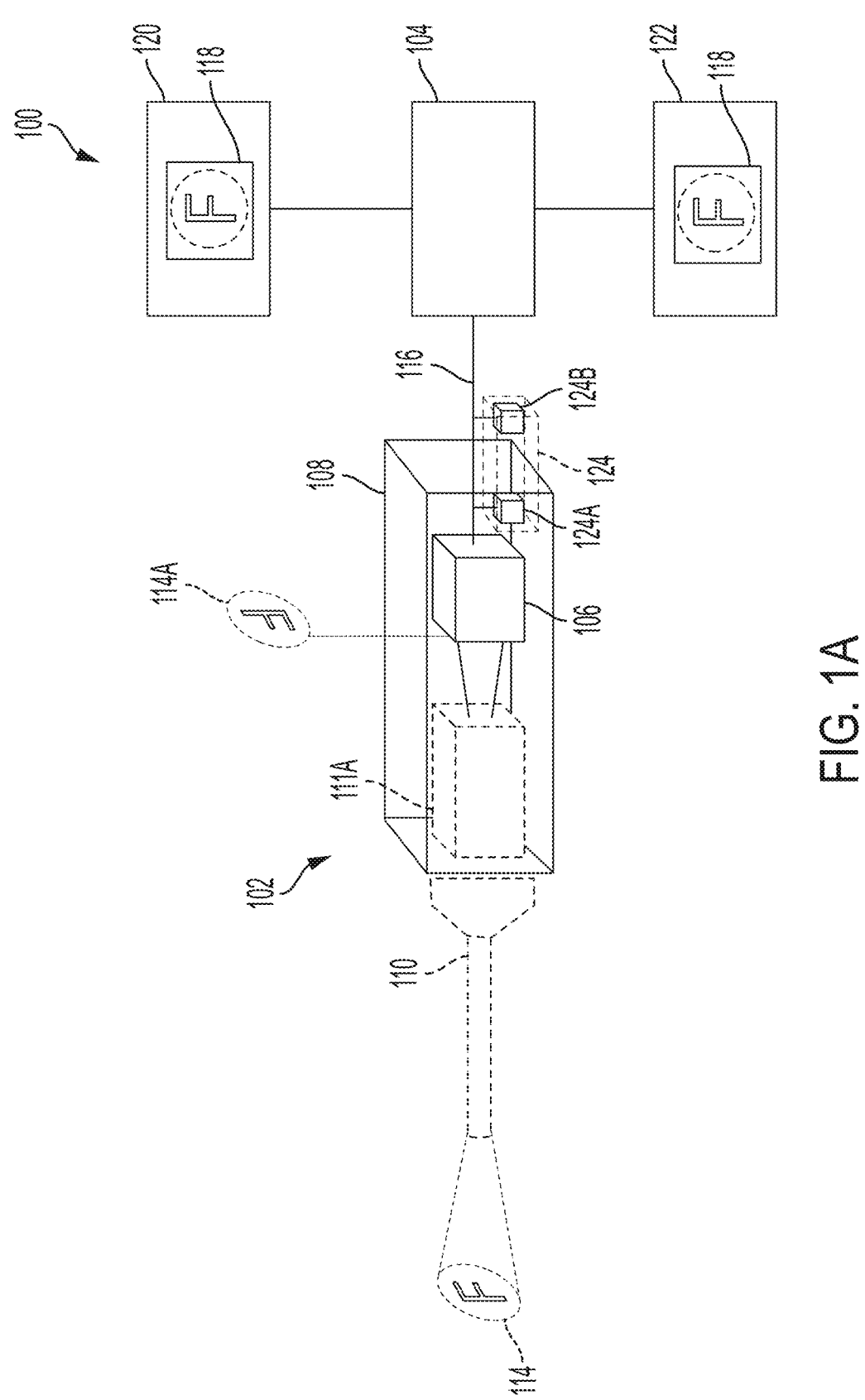
FIG. 1A illustrates a first embodiment of an endoscopic imaging system 100 in which an endoscope is mounted to a camera head in line with the imaging axis, according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are various embodiments of medical imaging systems and methods for generating images (which encompasses single images and video frames) with correctly oriented scenes in which the camera head is configured and/or oriented such that the scene is received at the imaging sensor in an incorrect orientation from the perspective of the user. According to various embodiments, a medical imaging system can include a camera head communicatively coupled to a camera controller that receives image data from the camera head and generates images for display and/or storage. The camera controller can receive configuration information from the camera head that indicates that the camera head is capturing a scene in an incorrect orientation. According to various embodiments, this configuration information can be static information, such as indicating that the camera head is configured to receive the scene at the imaging sensor in an incorrect orientation, and/or can be dynamic information that indicates a current orientation of the camera head.

In some embodiments, the camera controller controls the camera to transmit imaging data to the camera controller in such a way that that the scene is correctly oriented as received by the camera controller. For example, the camera controller can instruct the camera head to read pixels in reverse order relative to a conventional read order. In some embodiments, the camera controller can digitally process image data to reverse the relative locations of pixel values, which digitally flips the scene within the camera controller.

According to various embodiments, by configuring the camera controller and camera head so that the camera head is controlled and/or the image data from the camera head is processed to reorient the scene, a right-angle camera head can be configured with a right-angle prism, which reflects the light just once. This single reflection can lead to improved image quality relative to conventional camera heads that redirect 90° using multiple reflections—such as systems with pentaprisms and systems with roof prisms. Further, a right-angle prism can be easier to manufacture and less sensitive to tolerance than prism or prism systems that reflect light multiple times.

According to various embodiments, by configuring the camera controller and camera head so that the camera head is controlled and/or the image data from the camera head is processed to reorient the scene, the camera head can be used upside-down while maintaining a scene right-side-up. One or more orientation sensors can be included in the camera head and can provide orientation information from the camera head to the camera controller. When the camera head is being used upside-down, the camera controller can control the camera head and/or process imaging data so that the scene is reoriented, and when the camera head is being used right-side-up, the control and/or image processing can revert, for example, to a conventional process.

In the following description of the various embodiments, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Camera systems are conventionally configured to capture images of a scene in which the scene is oriented according to a user's point of view when using the camera. Therefore, when a camera is directed in a horizontal direction, the camera is configured so that an image captured by the camera will have the top of the scene at the top of the image. This is conventionally done by orienting the imaging sensor within the camera such that the "top" of the sensor receives light from the top of the scene. Thus, as used herein, an imaging sensor receiving a correctly oriented scene means that the top, bottom, left, and right portions of the scene are received by the top, bottom, left, and right portions, respectively, of the imaging sensor. Further, as used herein, an image having a correctly oriented scene means that the top, bottom, left, and right portions of the scene are the top, bottom, left, and right portions, respectively, of the image when viewed on a display.

As used herein, a misoriented scene is one that is not correctly oriented as defined above. A scene can be misoriented in different ways. As used herein, an inverted scene is one in which the scene is flipped 180° about a horizontal axis extending left-to-right. As used herein, a reverted scene is one in which the scene is flipped 180° about a vertical axis extending top-to-bottom. A scene can be both inverted and reverted, which results in a scene that is rotated 180° about a horizontal axis extending perpendicular to the scene.

Figure 1B:
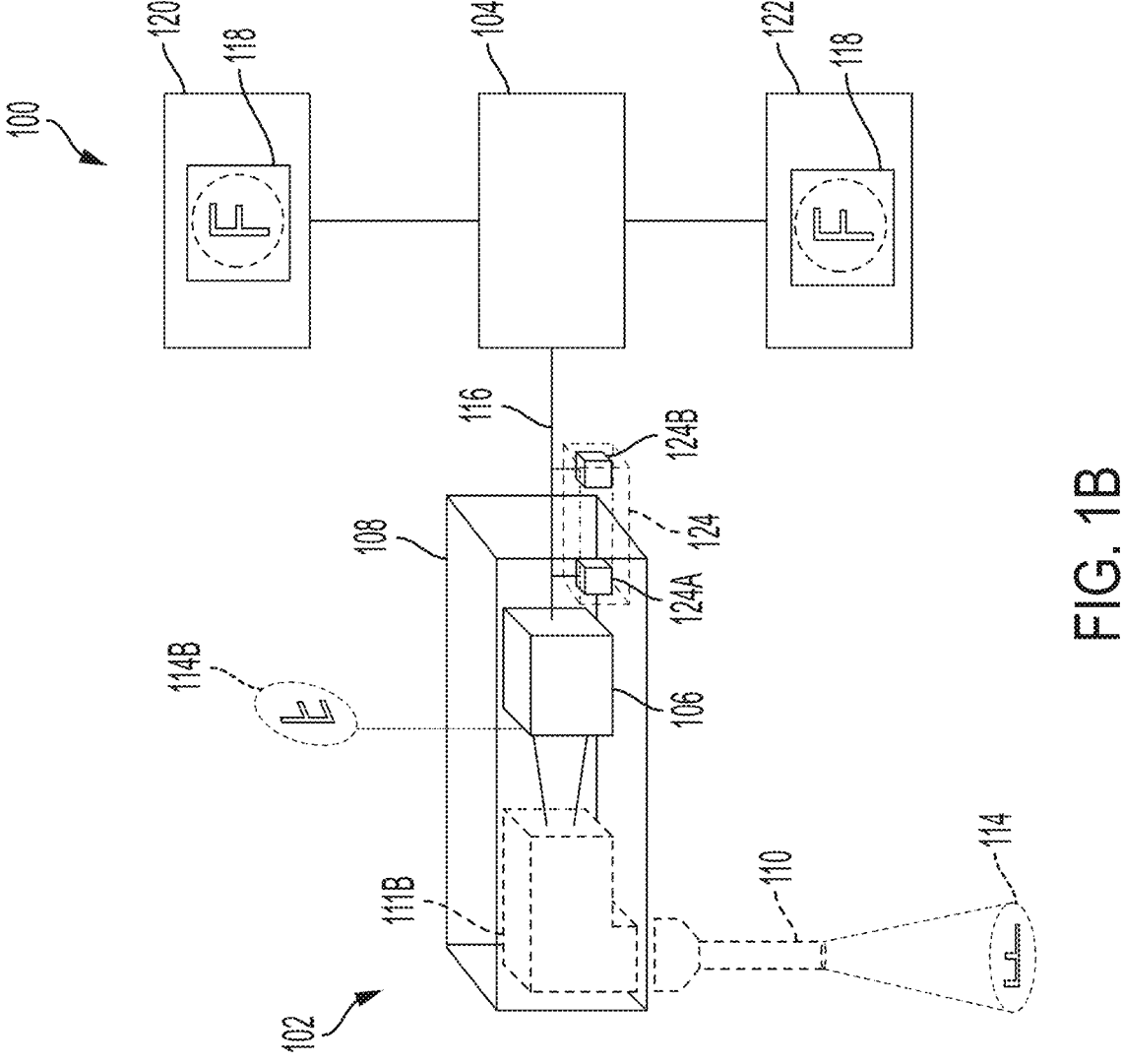
FIG. 1B illustrates a second embodiment of an endoscopic imaging system 100 in which an endoscope is mounted to a camera head perpendicularly to the imaging axis, according to some embodiments.

FIGS. 1A and 1B illustrate embodiments of an endoscopic imaging system 100. As discussed further below, FIG. 1A illustrates an embodiment of system 100 in which an endoscope is mounted to the camera head such that the endoscope is in line with the imaging axis and FIG. 1B illustrates an embodiment of system 100 in which the endoscope is mounted perpendicularly to the imaging axis.

Imaging system 100 includes an endoscopic camera unit 102 that includes an imaging sensor assembly 106 that captures a scene according to a first orientation and a camera controller 104 that can control the imaging sensor assembly 106 and/or process imaging data from the imaging sensor assembly 106 to reorient the scene relative to the orientation of the scene at the imaging sensor assembly 106. The ability to reorient the scene can provide a number of advantages, including simplified optics for embodiments in which the scene plane is perpendicular to the imaging plane of the imaging sensor assembly and the ability for the user to use the endoscopic camera unit 102 in an upside-down orientation while maintaining the orientation of the scene right-side-up on a display.

The endoscopic camera unit 102 can include a camera head 108 that includes the imaging sensor assembly 106. An endoscope 110 extends from the camera head 108 and, as is well-known in the art, can be inserted into a surgical cavity for imaging within the surgical cavity. The camera head 108 includes an endoscope coupling arrangement 111A,B that couples the endoscope 110 to the camera head 108. Two exemplary endoscope mounting configurations are illustrated. In FIG. 1A, the endoscope coupling arrangement 111A provides a straight-ahead mounting of the endoscope, such that the longitudinal axis of the endoscope is aligned with the imaging axis. In FIG. 1B, the endoscope coupling arrangement 111B provides a right-angle mounting of the endoscope 110 such that the longitudinal axis of the endoscope is perpendicular to the imaging axis, which may be advantageous for certain surgical procedures, such as for urology and/or ENT procedures. Camera heads that mount the endoscope at a right angle, such as via coupling 111B, is also referred to herein as a right-angle camera head.

The endoscope 110 includes a distal end that receives light from a scene 114. As is well-known in the art, light is communicated along the endoscope 110, such as via an assembly of lenses, to the imaging sensor assembly 106. The imaging sensor assembly 106 includes one or more imaging sensors that receive the light from the scene 114 at a plurality of pixels and generates pixel data. The pixel data from the one or more imaging sensors can be transmitted to the camera controller 104, such as via a cable 116 and/or wirelessly, and the camera controller 104 generates one or more images 118 (e.g., single images and video frames) from the pixel data. The image 118 may be stored in a storage medium 120 and/or may be displayed on one or more displays 122.

The scene 114 may be received at the imaging sensor assembly 106 in an incorrect orientation. For example, the top of the scene may be received at pixels of the imaging sensor assembly 106 that are associated with capturing a bottom of a scene and the bottom of the scene may be received at pixels of the imaging sensor assembly 106 that are associated with capturing a top of a scene.

Incorrect orientation of the scene 114 at the imaging sensor assembly 106 may be caused by, for example, the camera head 108 being used in an upside-down manner, which may be useful to a user when maneuvering an endoscope within the surgical cavity. As illustrated in FIG. 1A, an embodiment with an endoscope 110 mounted in line with the camera head 108 may view a scene. When the camera head is right side up, the scene 114 the correct orientation of the scene is captured by the imaging sensor assembly 106. However, when the camera head is used upside down, the imaging sensor assembly 106 captures the scene rotated 180° relative to the actual orientation of the scene, as indicated by rotated scene 114A.

In some embodiments, a scene can be misoriented due to reflection of light within the endoscopic camera unit 102. For example, as discussed further below, as illustrated in FIG. 1B, an endoscope 110 may be attached to a right angle camera head, one or more prisms or mirrors may be used to redirect the light 90°, and the redirection may result in the misorientation of the scene at the imaging sensor assembly 106, as indicated by inverted scene 114B.

The camera controller 104 can detect the configuration of the camera head 108 and correct scene orientation as needed. The camera controller 104 receives pixel data from the imaging sensor assembly 106 and generates an image of the scene. The camera controller 104 may control the imaging sensor assembly 106 so that the pixel data is received by the camera controller 104 from the imaging sensor assembly 106 according to the correct orientation and/or may modify the pixel data received from the sensor assembly 106 to generate an image with a correctly oriented scene. For example, the camera controller 104 may control the sensor assembly 106 such that pixels are read in reverse order by the one or more imaging sensors of the imaging sensor assembly 106 and/or the camera controller 104 may process the pixel data received from the sensor assembly 106 to swap pixels to re-orient the scene.

According to some embodiments, the camera controller 104 may receive information from the endoscopic camera unit 102 that indicates or is related to the orientation of the scene as captured by the imaging sensor assembly 106. In some embodiments, the scene orientation-related information can include camera unit configuration information, such as indicating that the camera unit 102 captures an incorrectly oriented scene at the sensor assembly 106—e.g., due to the endoscope being attached to a camera head 108 having a right angle endoscope coupling 111B. In some embodiments, the scene-orientation related information can include information regarding how the camera unit 102 is being used. For example, the information can indicate that the camera unit 102 is being used in an upside-down manner such that the scene is being captured by the sensor assembly 106 in an upside-down manner relative to the expectation of the user. In some embodiments, scene orientation-related information can include both configuration information i.e., right-angle configuration versus standard configuration—as well as use information, such as camera unit orientation.

According to some embodiments, a scene orientation information subsystem 124 may transmit scene orientation-related information to the camera controller 104, such as via cable 116, that indicates how the camera unit 102 is configured and/or is being used. For example, the scene orientation information subsystem 124 may transmit information indicating that the camera unit 102 is configured such that the scene is always inverted at the sensor assembly 106— e.g., due to the endoscope being attached to a right angle camera head. In some embodiments, the scene orientation information subsystem 124 may be configured to detect the orientation of the camera unit 102, such as via one or more gyroscopes and/or accelerometers, and may transmit orientation information to the camera controller 104 that indicates the current orientation of the camera unit e.g., upside down or right-side up. In some embodiments, the scene orientation information subsystem 124 provides both camera unit configuration information (e.g., right-angle camera) as well as camera unit orientation information (e.g., the camera unit is currently in an upside-down configuration). Based on the information received from the scene orientation information subsystem 124, the camera controller 104 may modify control of the sensor assembly 106 and/or may modify processing of pixel data received from the sensor assembly 106 to generate an image having a correctly oriented scene.

The scene orientation information subsystem 124 can include a single component or multiple interrelated or separate components. In some embodiments, the scene orientation information subsystem 124 is a memory, such as non-volatile memory, that stores configuration data, such as indicating that the camera unit is a right-angle camera unit. The configuration data stored in the memory can be transmitted to the camera controller 104 upon connection of the camera unit 102 to the camera controller 104, upon startup of the camera unit 102 when connected to the camera controller 104, continuously, or in any combination thereof. The configuration data stored in the memory can be accessed by one or more processors in the camera unit 102 or one or more processors in the camera controller 104. The memory can be housed in the camera head 108, in the cable 116 connecting the camera head 108 to the camera controller 104, or a combination thereof.

In some embodiments, the scene orientation information subsystem 124 includes multiple components, such as memory, one or more processors, and/or one or more sensors, for generating scene orientation-related information. For example, the scene orientation information subsystem 124 may include one or more orientation sensors (e.g., gyroscopes, accelerometers, etc.) controlled by one or more processors that generate orientation information from the one or more sensors. This information may be transmitted to the camera controller 104 in a continuous fashion so that the camera controller 104 knows when the orientation of the camera unit 102 has changed.

In some embodiments, the scene orientation information subsystem 124 includes multiple distinct sub-units that may or may not be interconnected. For example, in some embodiments, the scene orientation information subsystem 124 includes a memory storing camera unit configuration data and also includes a separate sensor unit that generates camera head orientation information. These sub-components may or may not be communicatively coupled to one another and may or may not be located in the same physical space. For example, as shown in FIG. 1A and FIG. 1B, a camera unit orientation sensor system 124a may be housed in the camera head 108, while memory 124b storing configuration data may be housed in the cable 116.

Figure 2A:
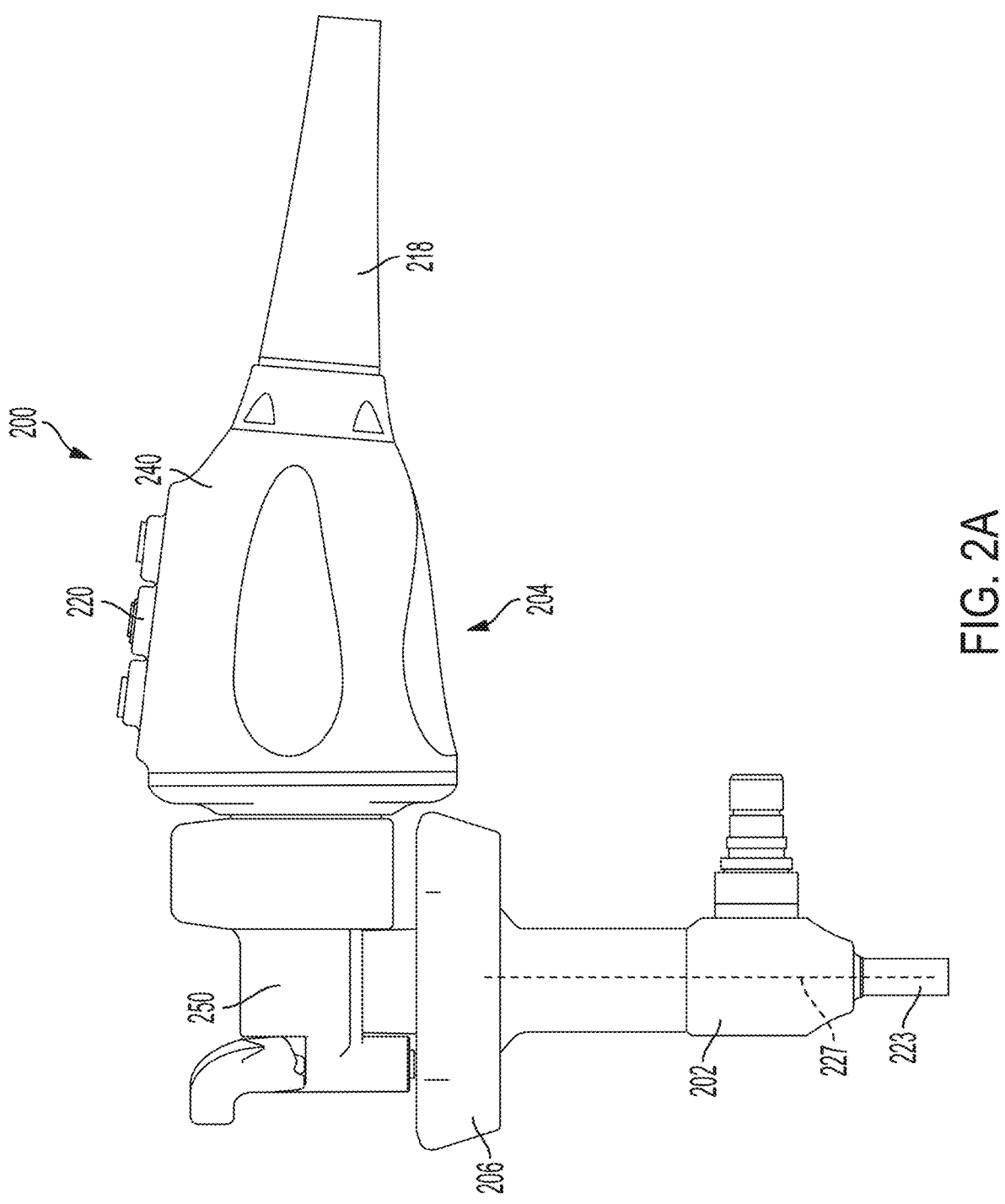
FIGS. 2A-2C illustrate an endoscopic camera unit that includes a camera head that mounts an endoscope in a right angle orientation relative to an imaging sensor assembly within the camera head, according to some embodiments.

FIG. 2A illustrates an endoscopic camera unit 200 that includes a camera head 204 that mounts an endoscope 202 in a right angle orientation relative to an imaging sensor assembly within the camera head 204. Camera unit 200 may be particularly suited for urological procedures in which the user often desires to orient the endoscope at a right angle relative to the camera head.

The optical components used in conventional right-angle camera head configurations may not transmit high quality images at high enough quality for the ever increasing resolutions available in imaging sensors, such as 4K imaging sensors. According to some embodiments, substantial optical improvement is achieved by using a right-angle prism to shorten the optical path length (the length that the image light must travel) and to minimize the amount of reflections, which can minimize losses and improve image resolution relative to conventional arrangements such as those using pentaprisms and roof prisms. Additionally, the right-angle prism is less prone to alignment errors during assembly than multi-reflection prisms, improving the repeatability and consistency of the image and reducing manufacturing costs.

However, using a right-angle prism requires that multiple "flips" be performed to regain the correct visual orientation of the scene in resulting images. Mechanical compensation (i.e. sensor mounting orientation) is not enough to reorient the image correctly. Therefore, as described further below, the endoscopic camera unit 200 can be connected to a camera controller, such as camera controller 104 of FIG. 1, which can control the camera unit 200 and/or processes pixel data from the camera unit 200 to generate an image having a correctly oriented scene.

The camera head 204 includes a first housing portion 240 that houses an imaging sensor assembly, which is discussed in more detail below. The first housing portion 240 can be sized and shaped for gripping and manipulating by a user, such as during a surgical procedure. The first housing portion 240 can include one or more user interfaces 220, such as one or more switches, buttons, sliders, touch screens, etc., for controlling one or more functions of the camera unit 200 and/or one or more functions of an imaging system to which the camera unit is operatively connected.

A second housing portion 250 extends from a distal end of the first housing portion 240. The second housing portion 250 can house one or more optical elements, as discussed further below. The second housing portion 250 may be assembled to the first housing portion to form a sealed enclosure to protect the sensitive imaging components within. The second housing portion 250 can be configured to mount the endoscope 202 in a right angle configuration relative to the optical axis of the imaging sensor assembly (see optical axis 273 in FIG. 2C).

A coupler 206 is mounted to the second housing portion 250 and is configured for coupling the endoscope 202 to the camera head 204. The coupler 206 can be any device suitable for attachment to an endoscope or other surgical viewing device. According to some embodiments, the coupler 206 is configured for removably coupling the endoscope 202, such as by including a spring-loaded structure for clamping the endoscope 202 to the camera head 204.

The endoscope 202 can be a conventional endoscope and generally includes an elongated shaft 223 that extends along a longitudinal axis 227. As is well known in the art, the shaft 223 can include an optical train comprised of one or more lenses, prisms, and/or other optical elements arranged to transmit light from a scene in a longitudinal direction from a distal end of the shaft 223. A light port (not shown) may be connected with light inputs to selectively transmit light to a target via the endoscope 202.

The camera head 204 may be connected or connectable to a camera cable 218 for connecting the camera unit 200 to a camera controller. The camera cable 218 can be removably or non-removably attached to the camera head 204. The camera cable 218 can transmit information, such as imaging data and/or user input data, to a connected camera control unit.

Figure 2B:
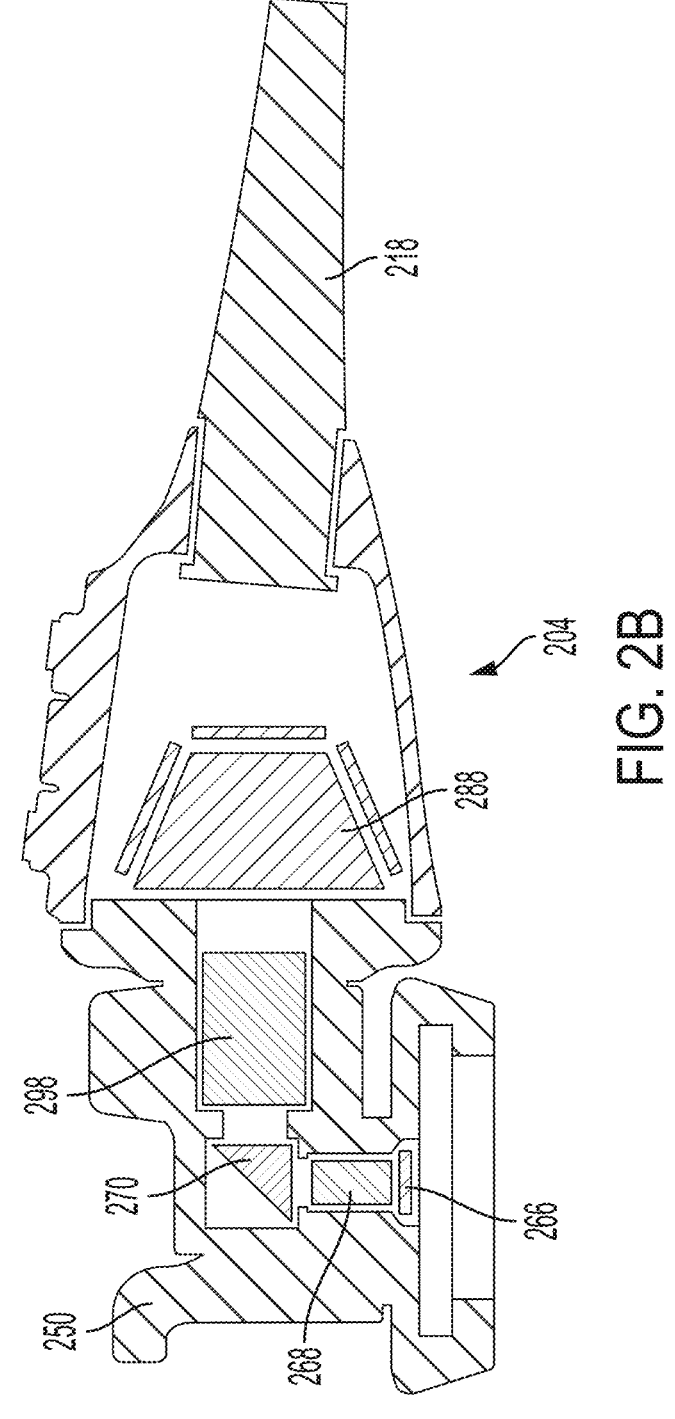
Figure 2C:
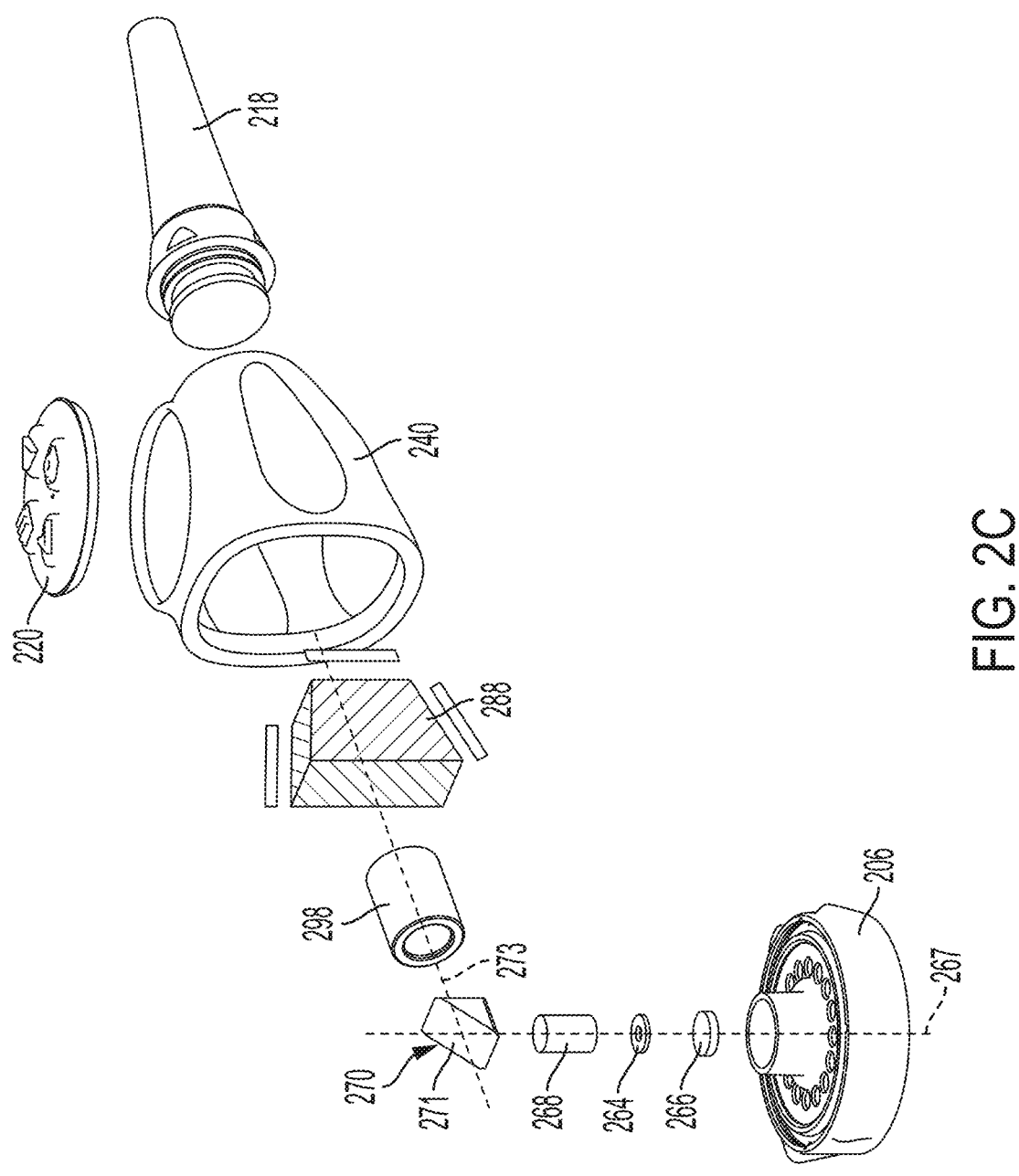

FIG. 2B is a cross sectional view of the endoscopic camera unit 200, according to various embodiments, illustrating optical components located in the first and second housing portions 240, 250. FIG. 2C is an exploded view of the endoscopic camera unit 200, according to various embodiments, with the second housing portion not shown for clarity.

The second housing portion 250 (see FIG. 2B) includes a light inlet aperture 264 that may receive a light inlet window 266. Light from a scene may be received from a connected endoscope via the light inlet window 266. The light inlet window 266 may be configured and mounted in the second housing portion 250 so as to seal the camera unit 200.

A relay lens assembly 268 may be mounted within the second housing portion 250 behind the light inlet window 266 for relaying the light along a first optical axis 267. The relay lens assembly 268 may include one or more lenses, filters, or other optical elements for manipulating the light received from the endoscope.

A prism 270 is mounted in the second housing portion 250 downstream of the relay lens assembly 268. The prism 270 redirects light traveling along the first optical axis 267 to a path extending along a second optical axis 273 toward an imaging sensor assembly 288. The prism 270 can be configured to redirect light off the long side 271 of the prism 270 such that the light is reflected only once by the prism 270. The long side 271 can be angled according to the desired redirection of the light. For example, the long side 271 can be angled at 45° relative to the first optical axis 267 to reflect the light at a right angle (as used herein, redirecting light at a right angle includes redirecting light substantially 90°, which can include redirecting light in a range between 80° and 100°. Because light is reflected only once by the prism, the scene is inverted by the prism 270, as discussed further below.

Light reflected by the prism 270 travels along the second optical axis 273 that extends at an angle—e.g., perpendicularly—to the first optical axis 267 through a lens system 298 that may be mounted in the second housing portion 250. The lens system 298 may include one or more lenses for focusing light onto an imaging sensor assembly 288. The lens system 298 may include one or more movable lenses for enabling user and/or automatic focusing. In some embodiments, light travels through the lens system 298 such that the scene is rotated 180° at the downstream end of the lens system 298 relative to the orientation of the scene at the upstream end of the lens system 298, as is well-known in the art. Accordingly, the imaging sensor assembly 288 may be rotated 180° relative to the orientation of the camera head to compensate for the 180° rotation of the scene by the lens system 298. In other embodiments, the lens system 298 may include one or more additional optical components that result in the same orientation of the scene at the downstream end relative to the upstream end of the lens system 298.

Light from the lens system 298 is received by the imaging sensor assembly 288, which may be housed in the first housing portion 240 and aligned with the second optical axis 273. The imaging sensor assembly 288 can include one or more imaging sensors for detecting light incident thereon. The one or more imaging sensors can include any suitable imaging sensor, such as CMOS and/or CCD imaging sensors. The imaging sensor assembly 288 can include one or more optical elements, including, for example, one or more lenses, prisms, filters, etc., for directing, shaping, and/or controlling the wavebands of light incident on the one or more imaging sensors. The imaging sensor assembly 288 can be fixedly mounted within the second housing portion 250, the first housing portion 240, or both, such that the one or more imaging sensor(s) are in fixed relationship with respect to the optical train upstream of the imaging sensor assembly 288.

The imaging sensor assembly 288 generates one or more imaging signals comprising pixel data that can be transmitted to a camera controller operatively coupled to the camera unit 200, such as via cable 218. According to various embodiments, the imaging sensor assembly 288 can generate and transmit single image and/or video data. The imaging sensor assembly 288 can include one or more processors for controlling and/or processing signals from the one or more imaging sensors. In some embodiments, the one or more processors can control the manner in which the pixel data is communicated from the camera unit 200 to an operatively coupled camera controller. For example, the one or more processors can control the imaging sensor assembly 288 to read-out pixels in reverse order, such as right-to-left instead of left-to-right. In some embodiments, the one or more processors can communicate with a connected camera controller to change pixel read-out modes. For example, the connected camera controller can control the one or more processors of the imaging sensor assembly 288 to change the read-out mode from a conventional mode to a reverse mode and vice versa.

Figure 3:
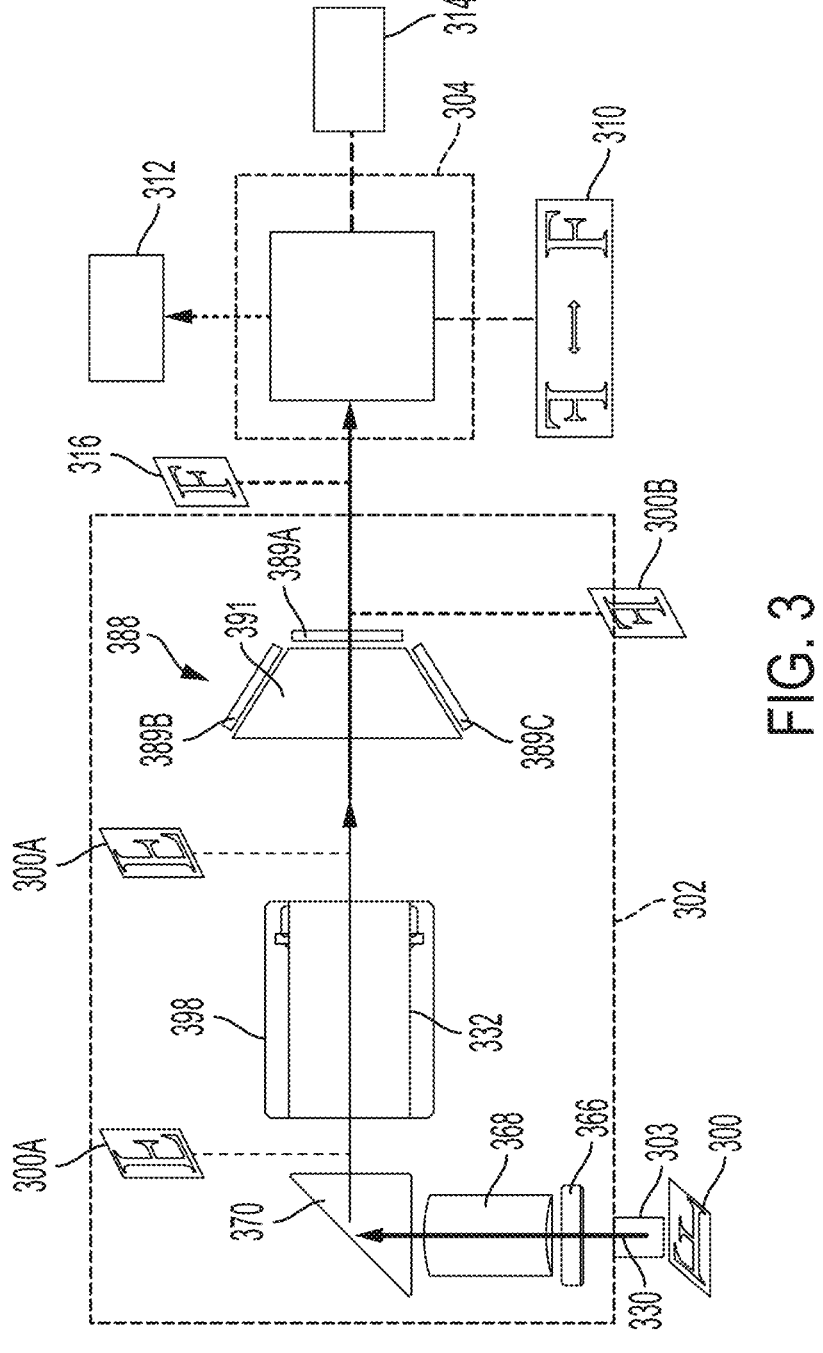
FIG. 3 illustrates the travel of a scene through an endoscopic imaging system having a camera head with a right-angle scope attachment, according to some embodiments.

FIG. 3 illustrates the travel of a scene 300 through an endoscopic imaging system having an endoscopic imaging unit 302 with a right-angle camera head, according to some embodiments. The endoscopic imaging unit 302, which can be configured like endoscopic camera unit 200 of FIGS. 2A-C, is connected to a camera controller 304. The endoscopic imaging unit 302 has a right-angle scope mounting configuration in which the endoscope 303 mounts to the imaging unit 302 at a right angle relative to an imaging sensor assembly 388 of the imaging unit 302.

The endoscopic imaging system is usable to image a scene 300, which can be, for example, a region of tissue in a surgical cavity. The region of tissue may reflect light delivered by a light delivery system of an endoscope and/or may emit light, such as from one or more fluorescence emitters (e.g., fluorescent dyes, autofluorescence, etc.), and the reflected and/or emitted light is received by the endoscope. Light from the scene 300 may travel in a first direction 330 through the endoscope, through window 366, and then through relay lens system 368 to right angle prism 370.

Right angle prism 370 redirects light in a second direction 332 toward the imaging sensor assembly 388. The right angle prism 370 reflects the light just once, and because of this single reflection, the scene becomes inverted—flipped 180° about a horizontal line extending midway across the scene—resulting in an inverted scene 300A. The inverted scene 300A travels through a lens system 398, which may deliver the inverted scene 300A to the imaging sensor assembly 388. In some embodiments, the lens system 398 may rotate the inverted scene 300A.

The imaging sensor assembly 388 can include any suitable number and type of imaging sensors. For example, a single imaging sensor may be used. In the illustrated embodiments, the imaging sensor assembly 388 includes three imaging sensors 389A,B,C to separately detect different light wavelengths. To divide and direct light received from the lens system 398, the imaging sensors 389 A,B,C are disposed on a beam splitting prism assembly 391. As is well known in the art, the prism assembly 391 can include filters for splitting the light into three different wavelength bands and directing the light according to its wavelength. For example, light can be split into red/IR light, green light, and blue light bands to provide fluorescent and white-light imaging. The three different wavelength bands are directed to the respective imaging sensors 389 A,B,C, which are each mounted so as to receive the scene in the same orientation.

The prism assembly 391 may be configured to reflect light toward the off-axis imaging sensors 389B and 389C. The prism assembly 391 may be configured to reflect the light such that the orientation of the scene at the interface between the respective imaging sensors 389 and the prism assembly 391 is the same as the orientation of the scene received from the lens system 398. For example, the prism assembly 391 may be configured such that the light path through the prism assembly 391 to each of the off-axis imaging sensors 389B,C includes two reflections, with the first reflection flipping the scene and the second reflection flipping the scene back. Thus, the orientation of the scene as presented to each sensor can be the same as the orientation of the scene as received by the prism assembly 391.

According to some embodiments, the imaging sensor assembly 388 may be configured such that the scene is received by the one or more imaging sensors 389 in a re-oriented manner relative to the inverted scene 300A. For example, the one or more imaging sensors 389 may be oriented upside down (as indicated in FIG. 3 by the + on bottom and the – on top), which effectively rotates the scene 180° as received by the one or more imaging sensors. This may result in a reverted scene 300B that is reverted relative to the scene 300—the scene is flipped 180° about a vertical line relative to the original scene 300. Thus, the scene as received by the one or more imaging sensors is in an incorrect orientation—e.g., reverted, as in the illustrated embodiment.

The imaging sensor assembly 388 generates pixel data that is transmitted from the endoscopic imaging unit 302 to the camera controller 304. The camera controller 304 can process the pixel data received from the endoscopic imaging unit 302 to generate one or more images of the scene for storage and/or display. According to various embodiments, the camera controller 304 can control the endoscopic imaging unit 302 and/or process pixel data from the endoscopic imaging unit 302 to generate an image with a correctly oriented scene.

In some embodiments, the camera controller 304, itself, processes the pixel data received from the imaging unit 302 to reorient the scene, as indicated by reference numeral 310. For example, the camera controller 304 may reverse the order of pixels within each row to flip the reverted scene 300B across a vertical line to a correctly oriented scene 300C. The camera controller 304 can manipulate the pixel data in any suitable manner, such as by rotating the scene, flipping the scene across a vertical line, and/or flipping the scene across a horizontal line.

In some embodiments, the camera controller 304 controls the endoscopic imaging unit 302 to transmit pixel data to the camera controller 304 in such a way that the camera controller 304 receives the pixel data according to a correct orientation of the scene, as indicated by reference numeral 316. For example, with respect to the reverted scene 300B, the camera controller 304 can instruct the endoscopic imaging unit 302 to read the pixel data from the one or more sensors 389A,B,C in reverse order relative to the conventional reading mode. For example, the pixels may be read across each row from right-to-left instead of left-to-right and transmitted in the sequence read. This can result in the scene being flipped right-to-left, which can result in a correctly oriented scene being transmitted from the endoscopic imaging unit 302 to the camera controller 304. Thus, the pixel data is received from the imaging unit 302 in accordance with a correctly oriented scene, and the camera controller 304 can process the pixel data in a conventional manner to generate an image with a correctly oriented scene.

In some embodiments, a reversed imaging sensor read mode is pre-programmed into the endoscopic imaging unit 302 so that pixel data is transmitted to the camera controller 304 according to reversed reading of the one or more sensors without involvement of the camera controller 304. However, providing the capability of the camera controller 304 to control the read mode of the one or more sensors can enable the same imaging sensor assembly (i.e., imaging sensor(s) and associated processing) to be used for different imaging units, such as both right-angled camera heads and straight camera heads.

The camera controller 304 can save one or more images (i.e., single images and video frames) with correctly oriented scenes to a memory 312, which can be a local or remote memory, and/or can transmit the one or more images with correctly oriented scenes to one or more displays 314 for display to a user.

FIG. 4 illustrates a method 400 for generating images having a correctly oriented scene by digitally reorienting the scene at the camera controller, according to some embodiments. Method 400 can be performed by a system that includes a camera unit that generates imaging data and transmits the imaging data to a connected camera controller, such as for example, system 100 of FIG. 1. Method 400 can be used for correcting the orientation of a scene captured by a right-angle camera head, such as camera head 204 of FIG. 2, and can be used for reorienting a scene resulting from using the camera head upside-down, as discussed further below with reference to FIGS. 6A and 6B.

At step 402, the camera controller receives configuration information from the camera unit. The configuration information may be stored in a computer readable medium, which may be located in the camera head, such as incorporated into the imaging sensor assembly of the camera head, or in a cable connecting the camera head to the camera controller. In some embodiments, the configuration information may be read directly by the camera controller from the storage in the camera head or camera cable. In some embodiments, the configuration information may be transmitted by a processor of the camera unit in response to a query/command received from the camera controller. The configuration information may indicate that the camera unit is a right-angle camera unit that captures a scene in an incorrect orientation. In some embodiments, the camera controller automatically receives configuration information from the camera unit. For example, upon connecting the camera unit to the camera controller (or upon powering up the camera unit and/or camera controller), the camera controller may query the configuration information unit in the camera unit for the configuration information.

At step 404, the camera unit images a scene and generates pixel data that it transmits to the camera controller. The camera unit may capture the scene at one or more imaging sensors in a misoriented manner due to reflection of light from the scene within the camera unit in such a manner that is not corrected via mounting of the imaging sensor(s). The pixel data transmitted to the camera controller, therefore, can include a misoriented scene.

At step 406, the camera controller receives the pixel data from the camera unit. The pixel data can be received via a cable connecting the camera head to the camera controller or can be received wirelessly. The pixel data may be received according to a misoriented scene. For example, in some embodiments, the scene as received by the camera controller may be in a reverted orientation—i.e., flipped about a vertical axis.

At step 408, the camera controller processes the pixel data to digitally reorient the scene to the correct orientation based on the configuration data received at step 402. Digitally reorienting the scene generally includes changing the relative positions of pixels within the data set. Pixel data received from a camera unit may be organized as a matrix of pixel intensities with the position of an intensity in the matrix corresponding to the position of the sensor pixel that generated the intensity in the imaging sensor assembly, and reorienting the scene can include swapping intensity values in the matrix. For example, the order of pixel values in each row of the matrix can be reversed to flip the scene about a vertical axis, and/or the order of pixel values in each column can be reversed to flip the scene about a horizontal axis. In some embodiments, the scene is reverted in the pixel data received from the camera unit and digitally reorienting the scene includes reversing the order of pixels within each row of the pixel matrix to flip the scene from a reverted scene to a properly oriented scene.

At step 410, an image (e.g., a single image or a video frame) with a properly oriented scene is stored and/or transmitted to a display for display to a user. The orientation of the scene in the image is the same as the orientation of the scene as received by the endoscope.

FIG. 5 illustrates a method 500 for generating images having correctly oriented scenes by modifying the camera unit operation such that the camera unit transmits image data to the camera controller in accordance with a correctly oriented scene, according to some embodiments. Method 500 can be performed by a system that includes a camera unit that generates imaging data and transmits the imaging data to a connected camera controller, such as for example, system 100 of FIG. 1. Method 400 can be used for correcting the orientation of a scene captured by a right-angle camera head, such as camera head 204 of FIG. 2, and can be used for reorienting a scene resulting from using the camera head upside-down, as discussed further below with reference to FIGS. 6A and 6B.

At step 502, the camera controller receives configuration data from the camera unit that indicates whether the camera unit receives an incorrectly oriented image at the imaging sensor(s) of the camera unit. This step may be similar to step 402 of method 400.

At step 504, in response to receiving configuration information indicating an incorrect scene orientation capture by the camera unit, the camera controller sends instructions to the camera unit to modify its operation so that the camera unit transmits pixel data in such a way that the camera controller receives a correctly oriented scene. The camera controller can send the instruction to the camera unit via a cable or wirelessly.

At step 506, in response to receiving the instructions from the camera controller, the camera unit can modify the manner in which it reads pixel data from the one or more imaging sensors. For example, the camera unit can read pixels in reverse order—e.g., from right to left instead of from left to right and/or from bottom to top instead of from top to bottom, such as by setting one or more register values according to a desired pixel read-out sequence. The camera unit then transmits the pixel data according to the modified reading procedure, which results in the camera controller receiving a scene that is flipped relative to the orientation in which it was captured by the one or more imaging sensors. For example, the scene may be reverted as captured by the one or more imaging sensors due to the inversion of the scene by the 90° prism following by rotation by the upside-down mounting of the imaging sensors and reversing the pixel readout procedure results in the reverted scene being flipped to the correct orientation.

At step 508, the pixel data that corresponds to a correctly oriented scene is received by the camera controller. The camera controller processes the incoming pixel data in a conventional manner to generate an image having the correctly oriented scene, at step 510. For example, the camera controller may conventionally generate an image by filling in the positions of an image matrix in the order that they are received from the camera unit. The camera controller may place the first pixel value in the upper left-hand corner of the image matrix, then fill in the remainder of the first row, fill in the second row in similar fashion, and continue in this manner until the last pixel value received from the camera unit for the given image or video frame is placed in the lower right-hand corner of the matrix. Due to the camera unit reading and transmitting the pixel values in each row in reverse, the camera controller places the pixel values generated by the right-most pixels of the one or more imaging sensors in the left-most positions of the image matrix, which results in a flipped scene relative to how the scene was captured by the one or more imaging sensors.

Thus, according to method 500, the reorienting of the scene can be done by the camera unit and the image processing by the camera controller can be conventional. In some embodiments, method 500 can also include a digital reorientation step by the camera controller. For example, the camera unit can perform a reverse reading step to flip the scene about a first axis and the camera controller can digitally flip the scene about a second axis.

The camera controller may be configured to operatively couple with conventional endoscopic camera units as well as camera units configured as described herein and can modify its imaging processing according to the type of camera unit that is connected to it. In accordance with the camera controller detecting that a connected camera unit is configured to capture a misoriented scene based on configuration data received from the camera unit and/or camera cable, the camera controller can proceed according to a first imaging process, such as described with respect to method 400 and/or method 500 above, to generate an image with a correctly oriented scene. In accordance with the camera controller detecting that a connected camera unit is configured to capture a correctly oriented scene based on configuration data received from the camera unit and/or camera cable, the camera controller can proceed according to a second imaging process that controls the camera unit and processes pixel data from the camera unit in a conventional manner. Thus, the camera controller can use different modes for controlling connected camera units based on the configuration data from the camera units. In some embodiments, when no configuration data is received from the camera unit, the camera controller may proceed according to the conventional mode.

Figure 6A:
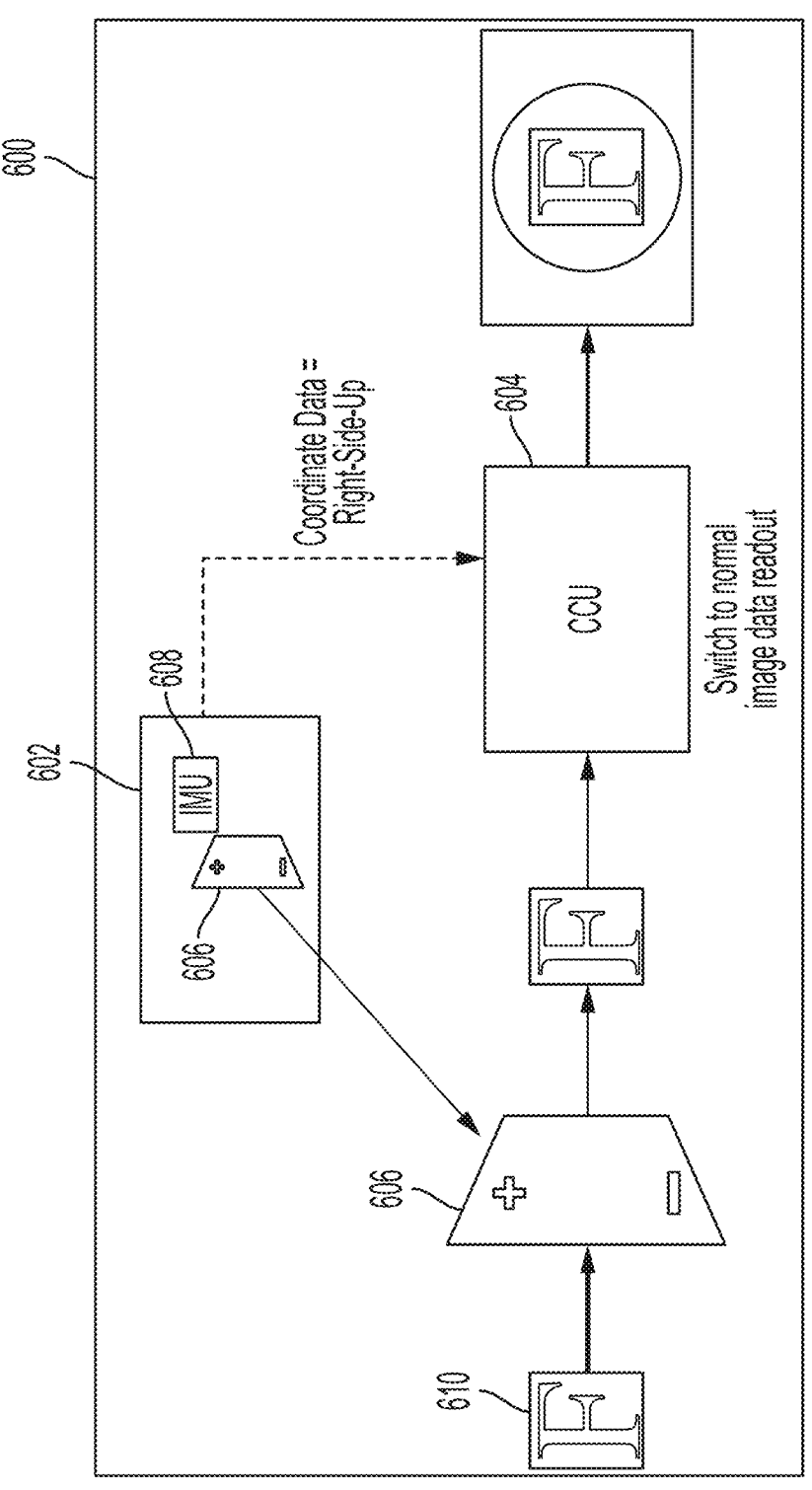
FIGS. 6A and 6B illustrate an imaging system in which the camera unit can be flipped upside down while automatically maintaining a right-side-up orientation of the scene in images generated from the camera unit, according to some embodiments.
Figure 6B:
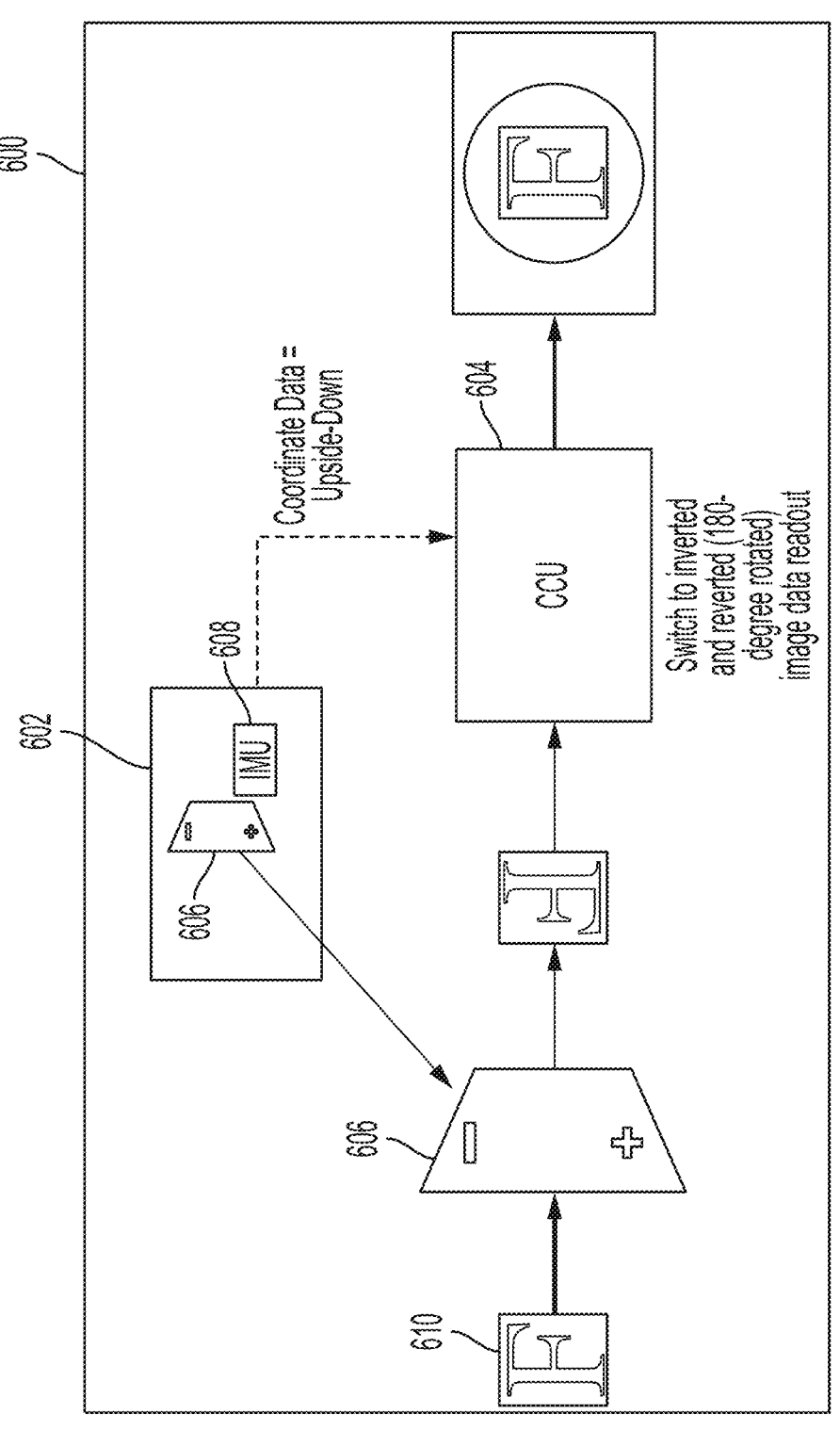

FIGS. 6A and 6B illustrate an imaging system 600 in which the camera unit can be flipped upside down while automatically maintaining a right-side-up orientation of the scene in images generated from the camera unit, according to some embodiments. The camera unit may include one or more sensors to detect the orientation of the camera unit and the connected camera controller may digitally process imaging data received from the camera unit to maintain scene orientation based on the camera unit orientation. For example, a user may turn the camera unit upside down and the camera controller may rotate pixel data received from the camera unit to generate images having the scene in a right side up orientation (i.e., right-side-up relative to the user).

Conventionally, an endoscopic camera system will display an image that is considered right-side-up when the camera head and internal imaging sensor is used in its designed right-side-up orientation. In some cases, endoscopic camera users may desire to turn the camera head upside-down to allow for easier access for surgical instruments or for more ergonomic grips. This is particularly advantageous for right-angle camera heads such as described herein where the right angle of the camera coupler causes the cable end of the camera head to point perpendicularly with respect to the endoscope axis, rather than more in line with the endoscope axis and pointing towards the user.

In conventional systems, as a result of turning the camera head and internal imaging sensor(s) upside-down, the scene orientation as it appears on the display will also be turned upside-down (or 180° rotated), which can cause user disorientation. Under these circumstances, a user may desire to reorient the display image to return the view to align with the user's right-side-up expectation. Conventionally, users have relied on manual methods for reorientation, including such methods as manually toggling the camera controller to digitally reorient the image, selecting an alternative display option on the monitor itself, or even physically turning the monitor upside-down.

According to various embodiments, a camera head and camera controller are configured to automatically reorient the scene in generated images relative to the orientation of the scene as captured by the one or more imaging sensors in order to maintain a right-side-up scene regardless of the right-side-up or upside-down orientation of the camera head. This can be advantageous over conventional systems since it can minimize user interactions to reorient the scene and/or avoid the complexity associated with camera heads having, for example, rotatable imaging sensors.

Imaging system 600 includes a camera unit 602 that includes an imaging sensor assembly 606 for imaging a scene. The imaging sensor assembly has a top side (+) and a bottom side (−). The camera unit 602 transmits imaging data to a camera controller 604, which generates one or more images (single images and/or video frames) from the imaging data.

The camera unit 602 includes a scene orientation information unit 608 for monitoring the orientation of the camera unit 602 and providing information related to the orientation of the camera unit 602 to the camera controller 604. The scene orientation information unit 608 can include one or more sensors for sensing changes in camera unit orientation. Any suitable sensors can be used, including any suitable combination of one or more accelerometers, gyroscopes, integrated units such as an inertial measurement unit (IMU), etc., for detecting changes in orientation of the camera unit. The scene orientation information unit 608 can include and/or interface with one or more processors for processing data from one or more sensors, such as for calculating camera unit orientation, and providing the data to the camera controller 604.

Information from the scene orientation information unit 608 is provided to the camera controller 604 so that the camera controller 604 can automatically reorient the scene based on changes in the camera unit orientation. In some embodiments, signals from one or more sensors of the scene orientation information unit 608 are provided to the camera controller 604 and the camera controller 604 determines the camera unit orientation. In other embodiments, the scene orientation information unit 608 performs its own orientation determination and provides an orientation status identifier to the camera controller 604—e.g., the camera unit informs the camera controller whether it is upside-down or right-side-up.

Based on information received from the one or more sensors, the camera controller 604 can automatically process the image data received from the camera unit 602 to reorient the scene relative to its orientation as captured by the one or more sensors when the sensor data indicates that the camera unit is upside-down. This image reorientation can be reversed if any subsequent changes in camera head orientation is detected (i.e. camera head is returned to right-side-up).

FIGS. 6A and 6B illustrate the process of generating an image with a scene that is automatically reoriented 180° when the camera unit 602 is turned upside down. Light from a scene 610 passes through the optical train of the camera unit 602 and is focused onto the imaging sensor assembly 606. The scene can be received at the imaging sensor assembly 606 according to the orientation in which it is received by the camera unit 602 or attached endoscope or can be received at the imaging sensor assembly 606 according to an incorrect orientation in accordance with the various embodiments described herein (e.g., due to a right-angle mounting of the endoscope to the camera head).

A user may orient the camera unit right-side up (FIG. 6A) or upside-down (FIG. 6B) relative to normal use. When oriented upside-down, the resulting image data from the imaging sensor assembly 606 is 180° rotated relative to the orientation when the camera unit is right-side up. The camera controller 604 receives orientation information from the camera unit 602 that indicates whether the camera unit is upside-down or right-side-up. In some embodiments, the camera unit 602 performs its own orientation determination and informs the camera controller 604 accordingly, while in other embodiments, the camera controller 604 makes its own determination based on sensor data from the camera unit 602, which can be, for example, three-dimensional position data provided by an inertial measuring unit (IMU) within the camera unit.

When the camera controller 604 establishes that the camera unit 602 is upside-down (FIG. 6B), the camera controller 604 can modify the image data read directionality to be inverted and reverted (180° rotated) from the normal image data read directionality. Alternatively, the camera controller 604 may digitally reorder the pixel data received from the camera unit to rotate the scene. The camera controller can then then output an image having a reoriented scene to the display and/or storage.

The camera controller 604 may receive camera unit orientation updates from the camera unit and, based on the updates, may determine that the camera head is returned to a right-side-up state and can revert the image data read directionality back to a previous directionality or revert the pixel data processing to a conventional mode. The camera controller 604 may switch between modes—i.e., reoriented and non-reoriented—according to any subsequent reorientations of the camera head.

The terms upside-down and right-side-up are used herein to refer to relative changes in orientation that trigger scene reorientation and are not meant to be limiting to only perfectly "upside-down" and right-side-up" orientations. For example, in some embodiments, the camera is considered to be in a given orientation with respect to the scene as long as the camera head is within a predetermined range of angular orientations. Movement of the camera head within the predetermined range, then, does not trigger reorientation of the scene, but movement of the camera head beyond the predetermined range would then trigger scene reorientation. For example, considering perfectly right-side-up as a 0° orientation, image reorientation may not be triggered as long as the camera head is within a range of +/−90° from 0° (i.e., closer to perfectly right-side-up that upside-down) and once the camera head is rotated beyond this range (i.e., closer to perfectly upside-down than right-side-up), the camera controller commands reorientation of the scene. Similarly, the scene may continue to be reoriented as long as the camera head is in the range of +/−90° from 180° and may only stop being reoriented once the camera head rotates beyond this range. These are merely exemplary thresholds, and the upper and lower thresholds that trigger scene reorientation may be set as desired.

In some embodiments, the scene reorientation trigger thresholds are relative to a current orientation. For example, scene reorientation may be triggered when the camera head rotates to within a predetermined range of the opposite orientation. For example, scene reorientation may be triggered when the camera head is rotated to within the range of +/−10° of 180° and the scene reorientation may be maintained until the camera head is rotated back to within the range of +/−10° of 0°. So, the orientation of the scene when the camera head is at 90°, for example, may vary depending on the previous scene reorientation. This may be advantageous in reducing the number of times that the displayed image is flipped from the perspective of the user.

According to some embodiments, the scene is oriented/re-oriented 180° relative to the orientation of the scene at the imaging sensor assembly. Therefore, the image(s) generated and/or displayed to the user will show the scene in the orientation that is received at the imaging sensor assembly as the camera head is rotated—i.e., the displayed scene will rotate with the camera head—until the predetermined threshold is reached, at which point the scene will rotate 180° relative to the orientation of the scene at the imaging sensor assembly. Thus, angular movement of the camera head will be observed by the user viewing the generated images. This is in contrast to image stabilization systems known in other fields, such as surveillance or filmmaking—in which a scene is maintained in a given orientation relative to the user regardless of how the camera head is moved.

Figure 7:
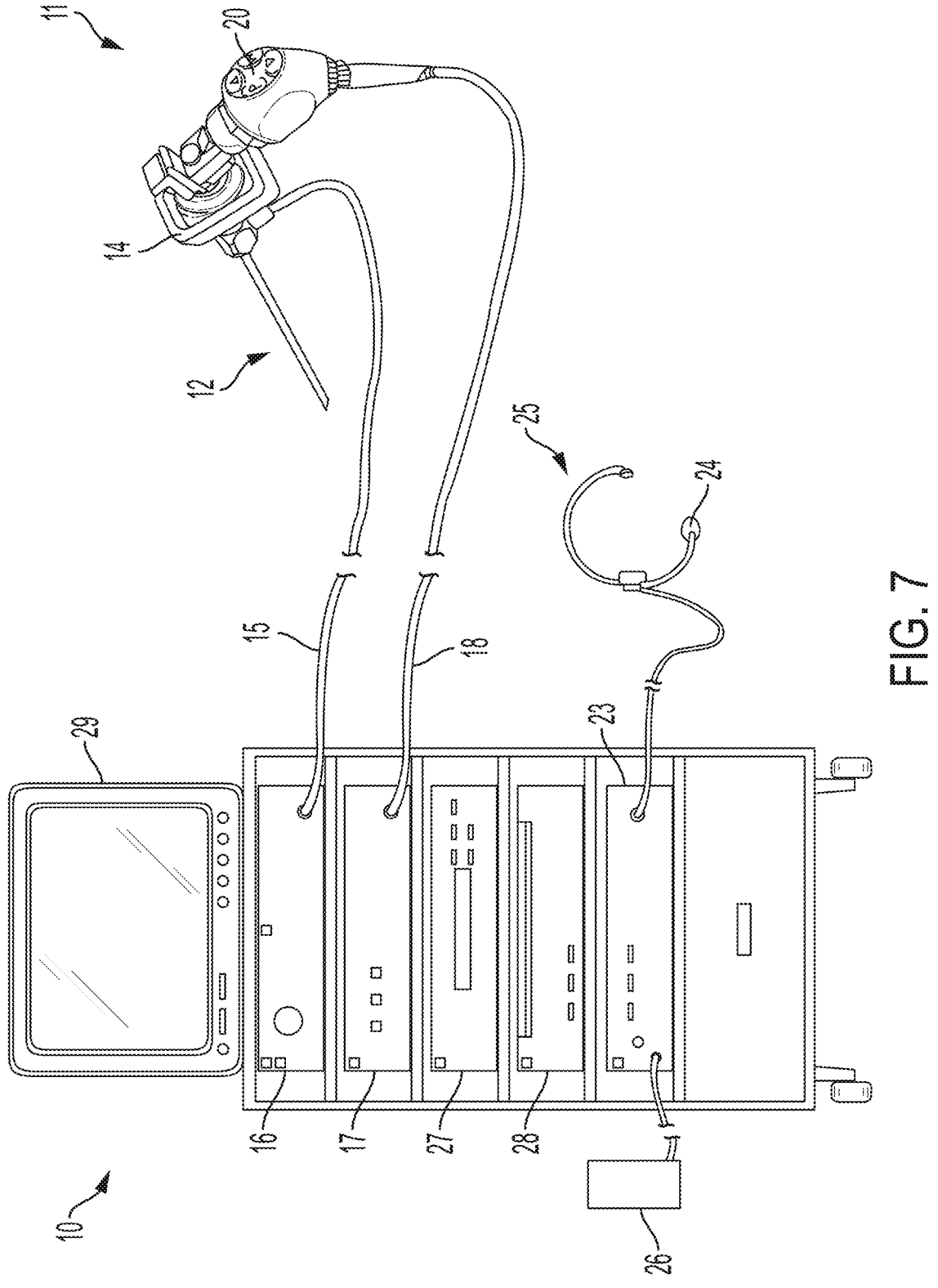
FIG. 7 illustrates an endoscopic imaging system, according to various embodiments.

FIG. 7 illustrates an endoscopic imaging system 10, according to various embodiments. The imaging system 10 includes an endoscopic imaging unit 11 that may be utilized in endoscopic procedures. The endoscopic imaging unit 11 can incorporate an endoscope or scope 12 coupled to a camera head 13 that has a coupler 14 located at the distal end of the camera head 13 for coupling the scope 12. The camera head 13 can be configured according to any of the embodiments described herein, including camera unit 102 of FIG.

1 and camera unit 200 of FIGS. 2A-2C. Light is provided to the scope 12 by a light source 16 via a light guide 15, such as a fiber optic cable. The camera head 13 is coupled to a camera controller 17, which can be configured according to any of the embodiments described herein, including camera controller 104 of FIG. 1 and camera controller 304 of FIG. 3. The camera head 13 can be coupled to the camera controller 17 via an electrical cable 18 or wirelessly. Operation of the camera head 13 can be controlled, in part, by the camera controller 17. The cable 18 or wireless communication system (not shown) conveys video or still image data from the camera head 13 to the camera controller 17 and conveys various control signals bi-directionally between the camera head 13 and the camera controller 17.

A control or switch arrangement 20 can be provided on the camera head 13 for a user to manually control various functions of the system 10. According to various embodiments, these and other functions may also be controlled by voice commands using a voice-control unit 23, which can be coupled to the camera controller 17. Optionally, voice commands can be input into a microphone 24 mounted on a headset 25 worn by the surgeon and coupled to the voice-control unit 23. A hand-held control device 26, such as a tablet with a touch screen user interface or a PDA, may be coupled to the voice-control unit 23 as a further control interface. In the illustrated embodiment, a recorder 27 and a printer 28 are also coupled to the camera controller 17. Additional devices, such as an image capture and archiving device, may be included in the system 10 and coupled to the camera controller 17. Video image data acquired by the camera head 13 and processed by the camera controller 17 is converted to images, which can be displayed on one or more displays 29, recorded by recorder 27, and/or used to generate static images, hard copies of which can be produced by printer 28.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A medical imaging system comprising:
   a camera assembly comprising:
      an imaging sensor assembly comprising at least one imaging sensor for imaging a scene;
      at least one focusing optical element for focusing light onto the imaging sensor assembly;
      at least one reflecting optical element for reflecting light received by the camera assembly from the scene toward the at least one focusing optical element, wherein reflecting the light causes the scene to be at least one of inverted and reverted at the imaging sensor assembly, and wherein the light from the scene is reflected only once before reaching the focusing optical element; and a camera controller configured to reorient the scene to generate a non-reverted and non-inverted image of the scene based on image data received from the imaging sensor, wherein the camera controller can save one or more images with correctly oriented scenes.

2. The system of claim 1, wherein the camera controller is configured to reorient the scene by controlling the camera assembly so that data is read from the at least one imaging sensor in reverse with respect to at least one dimension of the at least one imaging sensor.

3. The system of claim 1, wherein the camera controller is configured to reorient the scene by reordering the image data received from the imaging sensor to generate the non-reverted and non-inverted image of the scene.

4. The system of claim 1, wherein the camera controller is configured to detect a configuration of the camera assembly based on camera assembly configuration data stored in the camera assembly and generate the non-reverted and non-inverted image of the scene based on the camera assembly configuration data.

5. The system of claim 4, wherein the camera controller is connected via a cable to a camera head comprising the imaging sensor assembly and the camera assembly configuration data is stored in the cable or in the camera head.

6. The system of claim 1, wherein the one or more reflecting optical elements is configured to invert the scene.

7. The system of claim 6, wherein the imaging sensor assembly is configured so that the at least one imaging sensor receives a reverted scene.

8. The system of claim 1, wherein the one or more reflecting optical elements comprises a right angle prism.

9. The system of claim 1, wherein the camera assembly is configured for mounting a scope at a right angle orientation relative to an optical axis of the at least one focusing optical element.

10. The system of claim 9, wherein a camera head comprises the imaging sensor assembly and the endoscope is removably mounted to the camera head.

11. The system of claim 9, wherein, when the scope is mounted to the camera assembly, an optical axis of the scope is perpendicular to the optical axis of the at least one focusing optical element.

12. The system of claim 1, wherein the one or more reflecting optical elements is configured to reflect light at a right angle.

13. The system of claim 1, wherein the one or more reflecting optical elements is configured to reflect light at an angle that is in a range from 80° to 100°.

14. The system of claim 1, wherein the imaging sensor assembly comprises at least one prism for reflecting the focused light to the at least one imaging sensor.

15. The system of claim 1, wherein the system is an endoscopic imaging system, and the camera assembly is an endoscopic camera assembly that comprises an endoscope for receiving light from the scene.

16. A method for medical imaging, the method comprising:

receiving light from a scene at a camera assembly that comprises at least one reflecting optical element and an imaging sensor assembly;

reflecting light received by the camera assembly from the scene toward the imaging sensor assembly via the at least one reflecting optical element, wherein reflecting the light causes the scene to be at least one of inverted and reverted at the imaging sensor assembly, and wherein the light from the scene is reflected only once before reaching the focusing optical element;

focusing the reflected light onto the imaging sensor assembly with at least one focusing optical element;

transmitting image data generated from the focused light from the imaging sensor assembly to a camera controller;

reorienting the scene by the camera controller to generate a non-inverted and non-reverted image of the scene from the image data generated by the imaging sensor assembly; and saving by the camera controller the non-inverted and non-reverted image of the scene.

17. The method of claim 16, further comprising receiving camera configuration data at the camera controller and generating the non-inverted and non-reverted image of the scene based on the camera configuration data being indicative of incorrect orientation of the scene at the imaging sensor assembly.

18. The method of claim 16, wherein reorienting the scene comprises reading data from at least one imaging sensor of the imaging sensor assembly in reverse with respect to at least one dimension of the at least one imaging sensor.

19. The method of claim 16, wherein reorienting the scene comprises reordering the image data received from the imaging sensor to generate the non-reverted and non-inverted image of the scene.

20. The method of claim 16, comprising detecting a configuration of the camera assembly based on camera assembly configuration data stored in the camera assembly and generating the non-reverted and non-inverted image of the scene based on the camera assembly configuration data.

21. The method of claim 20, wherein the camera controller is connected via a cable to a camera head comprising the imaging sensor assembly and the camera assembly configuration data is stored in the cable or in the camera head.

22. The method of claim 16, wherein the one or more reflecting optical elements inverts the scene.

23. The method of claim 22, comprising receiving a reverted scene at the imaging sensor assembly.

24. The method of claim 16, wherein the one or more reflecting optical elements comprises a right angle prism.

25. The method of claim 16, wherein the camera assembly is configured for mounting a scope at a right angle orientation relative to an optical axis of the at least one focusing optical element.

26. The method of claim 25, wherein a camera head comprises the imaging sensor assembly and the endoscope is removably mounted to the camera head.

27. The method of claim 25, wherein, when the scope is mounted to the camera assembly, an optical axis of the scope is perpendicular to the optical axis of the at least one focusing optical element.

28. The method of claim 16, wherein the one or more reflecting optical elements is configured to reflect light at a right angle.

29. The method of claim 16, wherein the one or more reflecting optical elements is configured to reflect light at an angle that is in a range from 80° to 100°.

30. The method of claim 16, wherein the imaging sensor assembly comprises at least one prism for reflecting the focused light to the at least one imaging sensor.

* * * * *